(12) United States Patent
Yang et al.

(10) Patent No.: US 11,793,893 B2
(45) Date of Patent: Oct. 24, 2023

(54) COMPOUNDS COMPRISING CONDUCTIVE OLIGOMERS, MATERIALS FORMED THEREFROM, AND METHODS OF MAKING AND USING SAME

(71) Applicant: THE PENN STATE RESEARCH FOUNDATION, University Park, PA (US)

(72) Inventors: Jian Yang, Arlington, TX (US); Dingying Shan, University Park, PA (US)

(73) Assignee: THE PENN STATE RESEARCH FOUNDATION, University Park (PA)

( * ) Notice: Subject to any disclaimer, the term of this patent is extended or adjusted under 35 U.S.C. 154(b) by 567 days.

(21) Appl. No.: 16/337,469

(22) PCT Filed: Oct. 3, 2017

(86) PCT No.: PCT/US2017/055003
§ 371 (c)(1),
(2) Date: Mar. 28, 2019

(87) PCT Pub. No.: WO2018/067617
PCT Pub. Date: Apr. 12, 2018

(65) Prior Publication Data
US 2019/0231909 A1    Aug. 1, 2019

Related U.S. Application Data

(60) Provisional application No. 62/525,821, filed on Jun. 28, 2017, provisional application No. 62/403,224, filed on Oct. 3, 2016.

(51) Int. Cl.
| | | |
|---|---|---|
| *A61K 49/22* | (2006.01) | |
| *C08G 63/685* | (2006.01) | |
| *A61K 31/215* | (2006.01) | |
| *C08G 63/91* | (2006.01) | |
| *A61B 5/00* | (2006.01) | |
| *A61K 49/00* | (2006.01) | |

(52) U.S. Cl.
CPC .......... *A61K 49/222* (2013.01); *A61B 5/0095* (2013.01); *A61K 31/215* (2013.01); *A61K 49/005* (2013.01); *C08G 63/6854* (2013.01); *C08G 63/91* (2013.01)

(58) Field of Classification Search
CPC .............................. A61K 49/005; C08G 63/91
See application file for complete search history.

(56) References Cited

U.S. PATENT DOCUMENTS

| | | | | |
|---|---|---|---|---|
| 4,056,567 | A * | 11/1977 | Lamberti | ................ C07C 51/41 562/584 |
| 8,454,511 | B2 | 6/2013 | Milner et al. | |
| 8,921,429 | B2 | 12/2014 | Akai et al. | |
| 9,840,583 | B2 | 12/2017 | Yang et al. | |
| 2013/0029369 | A1* | 1/2013 | Adkins | .............. A61K 49/0002 435/29 |
| 2014/0311922 | A1 | 10/2014 | Ahrens et al. | |

FOREIGN PATENT DOCUMENTS

CN        103724620 A  *  4/2014

OTHER PUBLICATIONS https://en.wikipedia.org/wiki/Citric_acid, Printed From Web (Year: 2021).*
Gyawalli et al. "Citric acid-derived in situ crosslinkable biodegradable polymers for cell delivery", Biomaterials. Dec. 2010; 31(34): 9092-9105 (Year: 2010).*
Jin, et al. Multifunctional Nanoparticles as Coupled Contrast Agents, Nature Communications, vol. 1, Jul. 27, 2010, 41, pp. 1-17.
Llorens, et al. Nanomembranes and Nanofibers from Biodegradable Conducting Polymers, Polymers, vol. 5, Sep. 17, 2013.
International Search Report and Written Opinion dated Apr. 12, 2018 for PCT/US2017/055003.

* cited by examiner

*Primary Examiner* — James W Rogers
(74) *Attorney, Agent, or Firm* — Meunier Carlin & Curfman LLC

(57) ABSTRACT

A compound comprising an oligomer formed from a biocompatible multifunctional carboxylic acid comprising a hydroxyl group and at least one carboxylic acid, an polyol (e.g., an aliphatic diol), and a linker. One or more conductive oligomers (e.g., polyanilines) are covalently bonded to the oligomer. The compounds can have various forms (e.g., articles of manufacture, films, scaffolds, and the like). The compounds have various uses. For example, the compounds are used in photoacoustic imaging methods.

15 Claims, 27 Drawing Sheets

R1 = H, citric acid, or polymer chains;
R2 = H, citric acid, or polymer chains;
(due to the steric hindrance, R2 is generally H)
R3, R4 = OH, octanediol, citric acid* (very low possibility), AT, or polymer chains

AT =

Citric acid =

Citric acid* =

Octanediol = a (cont.)
Polymer chains can be any parts of the polymer, here are some examples:

a (cont.)

COMPOUNDS COMPRISING CONDUCTIVE OLIGOMERS, MATERIALS FORMED THEREFROM, AND METHODS OF MAKING AND USING SAME

CROSS REFERENCE TO RELATED APPLICATIONS

This application is a 35 U.S.C. § 371 National Stage filing of International Application No. PCT/US2017/055003, filed on Oct. 3, 2017, which claims priority to U.S. Provisional Application Ser. No. 62/403,224 filed Oct. 3, 2016 and U.S. Provisional Application Ser. No. 62/525,821 filed Jun. 28, 2017.

FIELD OF THE DISCLOSURE

The disclosure generally relates to compounds with conductive oligomeric groups. More particularly, the disclosure relates to use of the compounds in photoacoustic imaging.

BACKGROUND OF THE DISCLOSURE

Over the past decade, photoacoustic (PA) imaging, which is based on the absorption of optical energy to generate acoustic signals, has been highlighted as a powerful bioimaging technique due to its high spatial resolution, deep penetration depth, high contrast, non-ionizing radiation, and 3D structure generating ability. Many conducting polymers have strong optical NIR absorptions and can serve as PA contrast agents. This implies that biodegradable conducting polymers would also produce PA signals. Nevertheless, a single-modality imaging technique experiences limitations in certain situations. As a response to these limitations, multiple-modality imaging has recently drawn attention in biomedical research its ability to provide more comprehensive information. Fluorescence imaging is another technique that has been shown to produce good outcomes in biomedical studies and applications based on its cost effectiveness, use of maneuverable instruments, high temporal resolution, high sensitivity, and real-time imaging property. However, there are no suitable biodegradable conducting polymers for use in combining PA and fluorescent dual imaging. The present disclosure is pertinent to a need for improved biodegradable conducting polymers to serve as multifunctional tools for more precise and efficient diagnosis, treatment, and post-surgical detection.

SUMMARY OF THE DISCLOSURE

The present disclosure provides compositions and methods that relate to photoacoustic imaging. The methods generally comprise stimulating a composition of this disclosure, including but not limited to articles of manufacture coated with and/or impregnated and/or formed from the compositions, wherein the stimulation comprises a suitable form of light, and detecting an acoustic signal generated by the composition, and optionally detecting a fluorescent signal from the composition. The acoustic signal can be processed to, for example, generate an image.

The compositions comprise citrate-based elastic biodegradable photoluminescent polymers, or oligomers (e.g., BPLPs), possessing inherent photoluminescent properties that have been combined with aniline tetramer (AT) during the material synthesis processes to provide a biodegradable dual-modal photoacoustic/fluorescent imaging guided compound (e.g., BPLPAT), and thus imparting the capability of photoacoustic detection of the materials. Methods of making and using compounds (e.g., BPLPATs) are accordingly aspects of this disclosure. Compounds (e.g., BPLPATs) are expected to serve as an improved material platform with biodegradability, electrical conductivity, dual imaging capabilities, and tunable mechanical properties for use in a multitude of potential applications, such as tissue engineering, drug delivery, cancer treatment, and biosensing.

In an aspect, the present disclosure provides compounds. The compounds can be referred to as prepolymers that may be crosslinked to form elastomers (e.g., electroactive elastomers) or plastic materials (e.g., electroactive plastic materials). The compounds can also be referred to as aliphatic biodegradable conductive photoluminescent polymers. In an example, the compounds comprise an oligomer backbone (e.g., BPLP backbone) and one or more conductive oligomer (e.g., AT) covalently bonded to the oligomer backbone (e.g., BPLP backbone) (e.g., covalently bonded via an amide linkage pendant to the backbone of the oligomer) and/or one or more termini of the oligomer backbone (e.g., BPLP backbone) (e.g., covalently bonded via an amide linkage terminating the oligomer).

In various examples, a compound comprises an oligomer (e.g., a degradable oligomer), where the oligomer is synthesized from i) a biocompatible multifunctional carboxylic acid comprising a hydroxyl group and at least one carboxylic acid; ii) polyol (e.g., aliphatic polyol or aryl polyol); iii) a linker compound comprising an amine group; and iv) one or more conductive oligomers, where the one or more conductive oligomer is covalently bonded as a side group pendent to the oligomer backbone and/or one or more termini of the oligomer. The oligomer has a fluorescent cyclic moiety (e.g., a fluorescent monocyclic moiety or fluorescent bicyclic moiety) covalently bonded as a side group pendent to the oligomer backbone and/or covalently bonded as a moiety within the oligomer backbone that is formed from the biocompatible multifunctional carboxylic acid and the linker compound.

In an aspect, the present disclosure provides methods of making compounds of the present disclosure. The methods can be used to make a compound of the present disclosure. In various examples, a compound is made by a method of the present disclosure. The methods based on a "one-pot" synthesis where one or more linker compound, one or more biocompatible multifunctional carboxylic acid, one or more aliphatic diol, one or more conductive oligomer are combined. Alternatively, the methods are based on reaction of a precursor oligomer (e.g., a BPLP polymer) and one or more conductive oligomer.

In an aspect, the present disclosure provides uses of compounds of the present disclosure. For example, an article of manufacture comprises one or more compound of the present disclosure. Compounds of the present disclosure can be used in imaging methods. The imaging methods can be photoacoustic imaging methods, fluorescence imaging methods, or a combination thereof.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
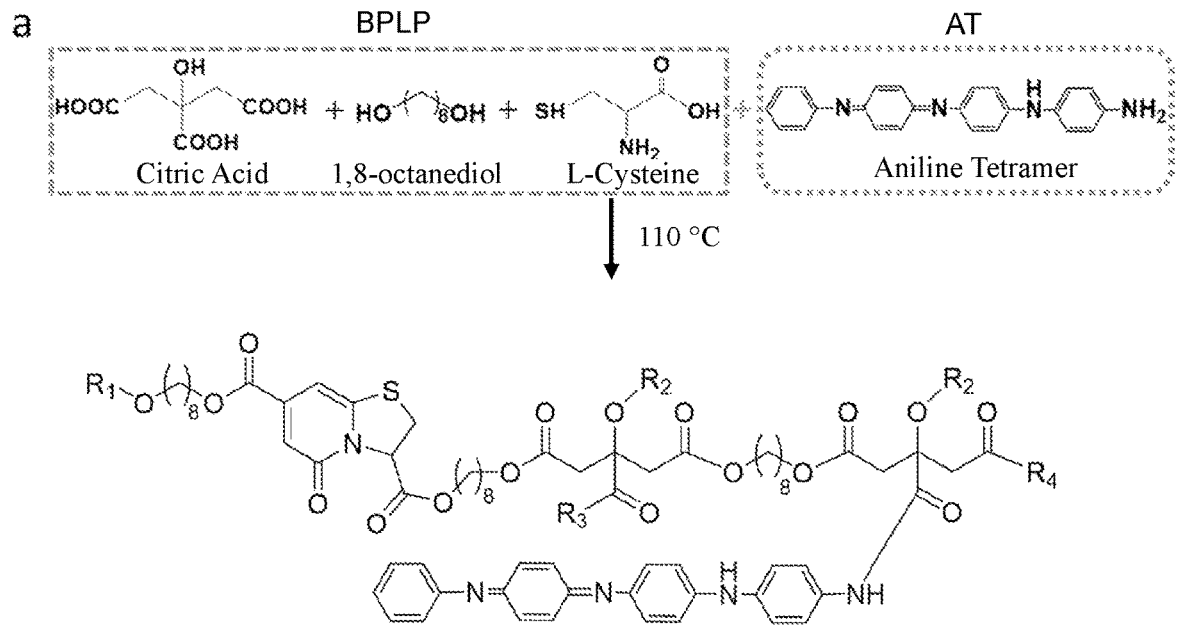
FIG. 1 shows synthesis of BPLPAT prepolymers. (a) Schematic synthesis of BPLPAT prepolymers. (b) FT-IR spectra of BPLPAT prepolymers. (c) $^1$H NMR spectrum of BPLPAT prepolymers.
Figure 1:
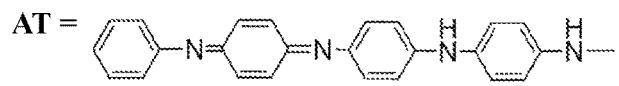
Figure 1:
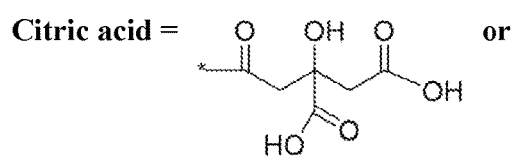
Figure 1:
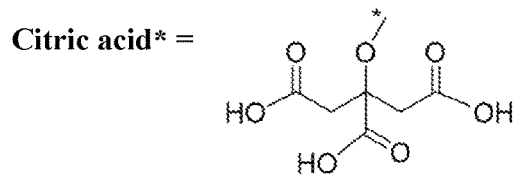
Figure 1:
Figure 1:
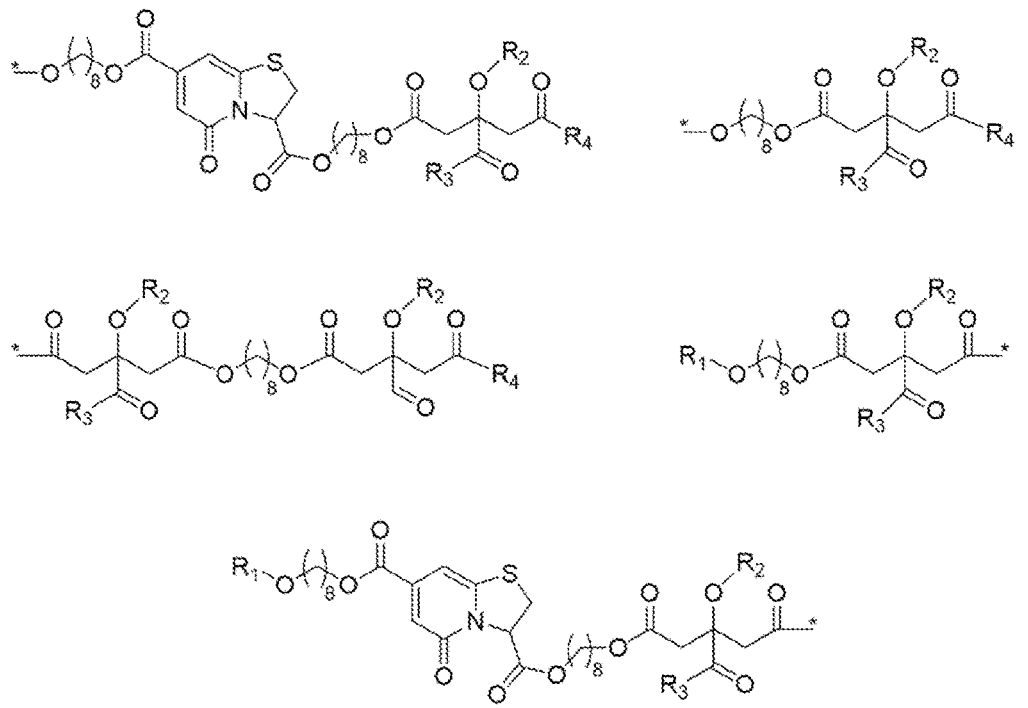
Figure 1:
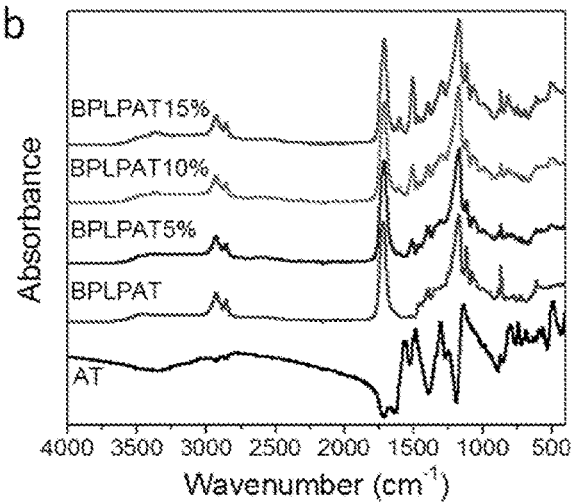
Figure 1:
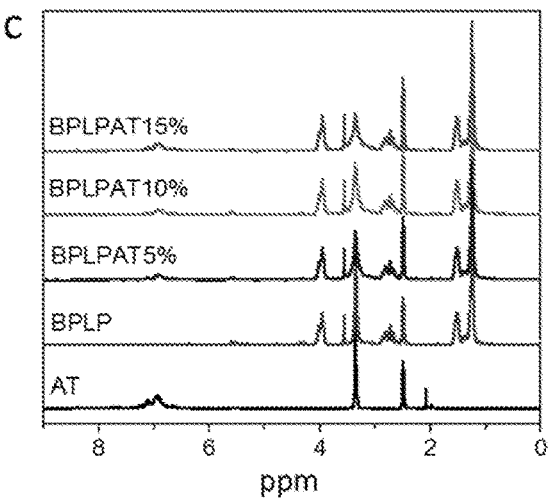

Although claimed subject matter will be described in terms of certain embodiments and examples, other embodiments and examples, including embodiments and examples that do not provide all of the benefits and features set forth herein, are also within the scope of this disclosure. Various structural, logical, and process step changes may be made without departing from the scope of the disclosure.

Every numerical range given throughout this specification includes its upper and lower values, as well as every narrower numerical range that falls within it, as if such narrower numerical ranges were all expressly written herein. All compositions of matter, all methods, and each step of each method disclosed herein are encompassed by this disclosure. The compounds, compositions comprising them, methods of making the compounds, and all uses of the compounds described herein, including in the form or methods, are included in this disclosure. Kits comprising compounds of this disclosure and containers containing the compounds, and instructions for using the compounds are included.

The disclosure includes all mechanical, electrical, and chemical properties of the compositions described herein, including but not limited to component ratios, and all in vitro and in vivo parameters described herein.

As used herein, unless otherwise stated, the term "group" refers to a chemical entity that has one terminus that can be covalently bonded to other chemical species. Examples of groups include, but are not limited to:

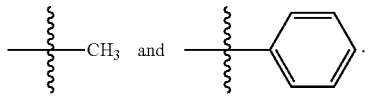

As used herein, unless otherwise stated, the term "moiety" refers to a chemical entity that has two or more termini that can be covalently bonded to other chemical species. Examples of moieties include, but are not limited to:

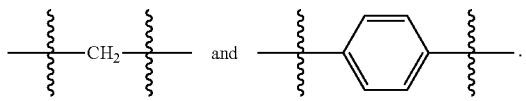

As used herein, unless otherwise indicated, the term "aliphatic" refers to branched or unbranched hydrocarbon groups/moieties that, optionally, contain one or more degrees of unsaturation. Degrees of unsaturation include, but are not limited to, alkenyl groups/moieties, alkynyl groups/moieties, and cyclic aliphatic groups/moieties. For example, the aliphatic group is a $C_2$ to $C_{30}$, including all integer numbers of carbons and ranges of numbers of carbons therebetween, aliphatic group. The aliphatic group can be unsubstituted or substituted with one or more substituent. Examples of substituents include, but are not limited to, various substituents such as, for example, halogens (—F, —Cl, —Br, and —I), additional aliphatic groups (e.g., alkenes, alkynes), aryl groups, alkoxides, carboxylates, carboxylic acids, ether groups, thiols, amines, and the like, and combinations thereof.

As used herein, unless otherwise indicated, the term "aryl" refers to aromatic or partially aromatic carbocyclic groups/moieties. For example, an aryl group/moiety is a $C_5$ to $C_{14}$, including all integer numbers of carbons and ranges of numbers of carbons therebetween, aryl group/moiety. The aryl group can comprise polyaryl moieties such as, for example, fused rings or biaryl moieties. The aryl group can be unsubstituted or substituted with one or more substituent. The aryl group can be a heteroaryl group. Examples of substituents include, but are not limited to, various substituents such as, for example, halogens (—F, —Cl, —Br, and —I), aliphatic groups (e.g., alkenes, alkynes), aryl groups, alkoxides, carboxylates, carboxylic acids, ether groups, and the like, and combinations thereof. Examples of aryl groups/moieties include, but are not limited to, phenyl groups/moieties, biaryl groups/moieties (e.g., biphenyl groups/moieties), and fused ring groups/moieties (e.g., naphthyl groups/moieties).

As used herein, unless otherwise indicated, the term "amino acid" refers to canonical and non-canonical amino acids, residues and monomers thereof, and combinations thereof. Canonical amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Non-canonical amino acids include, but are not limited to, selenocysteine, pyrrolysine, ornithine, D-amino acids, D,L-amino acids, L-β-amino acids, D-β-amino acids, D,L-β-amino acids, L-γ-amino acids, D-γ-amino acids, D,L-γ-amino acids, L-δ-amino acids, D-δ-amino acids, and D,L-δ-amino acids. In some instances, an α-amino acid includes an alkyl-substituted α-amino acid, such as a methyl-substituted amino acid derived from any of the "standard" or proteinogenic amino acids, such as methyl serine. An amino acid may be of Formula (F):

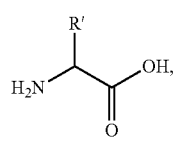

(F)

where R' is an amino acid side chain.

As used herein, unless otherwise indicated, the term "aminothiol" refers to β and γ-aminothiol groups/moieties. An aminothiol group/moiety comprises at least one amine group/moiety, at least one aliphatic group/moiety and/or at least one aryl group/moiety, and at least one thiol group/moiety. Examples of aminothiols include, but are not limited to, cysteine, cysteamine, 2-aminothiophenol, and derivatives and combinations thereof.

As used herein, unless otherwise indicated, the term "aliphatic amine" refers to branched or unbranched hydrocarbon groups/moieties terminating with an amine, where, optionally, the aliphatic portion contains one or more degrees of unsaturation. Degrees of unsaturation include, but are not limited to, alkenyl groups/moieties, alkynyl groups/moieties, and cyclic aliphatic groups/moieties. An aliphatic amine comprises at least one amine group/moiety and at least one aliphatic group/moiety.

As used herein, unless otherwise indicated, the term "aryl amine" refers to a group/moiety having at least one aryl group/moiety and at least one amine group/moiety.

The present disclosure provides compounds, methods of making the compounds. The present disclosure also provides uses of the compounds.

The present disclosure provides, in various examples, multifunctional carboxylate-based, e.g., citrate-based, elastic biodegradable photoluminescent polymers (BPLPs, e.g., an oligomer), possessing inherent photoluminescent properties that have now been combined with conductive oligomers, e.g., an aniline tetramer (AT), during the material synthesis processes to provide, in various examples, biodegradable dual-modal photoacoustic/fluorescent imaging guided compounds (e.g., BPLPATs), thus imparting the capability of photoacoustic detection of the materials. Methods of making and using compounds (e.g., BPLPATs) are accordingly aspects of this disclosure. BPLPs are described in U.S. Pat. No. 8,530,611, titled Biodegradable Photoluminescent Polymers, the disclosure of which is incorporated herein by reference.

This disclosure describes, in various examples, the development of a novel intrinsically electroactive biodegradable photoluminescent compounds and polymers (e.g., elastomers/plastic materials) via a novel method and their applications in optical imaging, tissue engineering, drug delivery, and other areas. The combination of BPLP and conductive oligomers (e.g., aniline tetramer (AT)) during the material synthesis processes significantly increases the solubility of conductive materials, obtained compounds (e.g., BPLPATs) are able to be dissolved in most organic solvents, such as, for example, dioxane, ethanol, and acetone. A novel catalyst-free thermal polycondensation reaction also endows intrinsically photoluminescent properties to electroactive polymers without using any traditional photobleaching fluorescent organic dyes or toxic quantum dots. On the other hand, for example, the rigid conductive oligomer (e.g., AT) structure can successfully balance the weak mechanical properties of BPLP, and resulting compounds (e.g., BPLPATs) have tunable mechanical properties from elastomers to plastics. In addition, a conductive oligomer (e.g., AT) is able to work as a buffer to reduce BPLP degradation acidity which strongly limited their biomedical applications. Compound (e.g., BPLPAT) films can promote nerve cell proliferation and differentiation, especially under electrical stimulation, which suggests that the compounds (e.g., BPLPATs) are potential for in vivo nerve regeneration. With photoluminescent and electrochemical properties, nanoparticles comprising a compound of the present disclosure (e.g., BPLPAT nanoparticles) can be used for cell labeling and controllable drug release for both in vitro and in vivo imaging and drug delivery purposes. With modification of specific targeting molecules, nanoparticles comprising a compound of the present disclosure (e.g., BPLPAT nanoparticles) are able to conducting targeted drug delivery and molecular bioimaging applications. Compounds (e.g., BPLPATs) can also be conjugated or synthesized into other materials or surfaces to make new families of electroactive photoluminescent materials. Thus, it will be recognized by those skilled in the art, given the benefit of the present disclosure, that the compounds (e.g., BPLPATs) and methods of this disclosure can be widely used in a broad range of biomedical applications including but not limited to tissue engineering, drug delivery, bioimaging, biosensoring, fluorescent labeling agents, etc., and can be implemented in human and non-human organisms (including but not limited to microbiological, virology, plant, animal, and mammalian (human and veterinary) approaches.

In an aspect, the present disclosure provides compounds. The compounds can be referred to as prepolymers that may be crosslinked to form elastomers (e.g., electroactive elastomers) or plastic materials (e.g., electroactive plastic materials). The compounds can also be referred to as aliphatic biodegradable conductive photoluminescent polymers. In an example, the compounds comprise an oligomer backbone (e.g., BPLP backbone) and one or more conductive oligomer (e.g., AT) covalently bonded to the oligomer backbone (e.g., BPLP backbone) (e.g., covalently bonded via an amide linkage pendant to the backbone of the oligomer) and/or one or more termini of the oligomer backbone (e.g., BPLP backbone) (e.g., covalently bonded via an amide linkage terminating the oligomer).

In various examples, a compound comprises an oligomer (e.g., a degradable oligomer), where the oligomer is synthesized from i) a biocompatible multifunctional carboxylic acid comprising a hydroxyl group and at least one carboxylic acid; ii) polyol (e.g., aliphatic polyol or aryl polyol); iii) a linker compound comprising an amine group; and iv) one or more conductive oligomers, where the one or more conductive oligomer is covalently bonded as a side group pendent to the oligomer backbone and/or one or more termini of the oligomer. The oligomer has a fluorescent cyclic moiety (e.g., a fluorescent monocyclic moiety or fluorescent bicyclic moiety) covalently bonded as a side group pendent to the oligomer backbone and/or covalently bonded as a moiety within the oligomer backbone that is formed from the biocompatible multifunctional carboxylic acid and the linker compound.

In various examples, a compound comprises an oligomer, where the oligomer is synthesized from i) a biocompatible multifunctional carboxylic acid comprising a hydroxyl group and at least one carboxylic acid; ii) an polyol (e.g., aliphatic polyol or aryl polyol), iii) a linker, and iii) one or more conductive oligomers. The one or more conductive oligomers can be part of the oligomer synthesis or added to a pre-synthesized BPLP oligomer.

Various biocompatible multifunctional carboxylic acids can be used. A biocompatible multifunctional carboxylic acid has at least one carboxylic acid/carboxylate functional group and at least one hydroxyl group. Non-limiting examples of biocompatible multifunctional carboxylic acids include citric acid, tricarballylic acid, aconitic acid, citraconic acid, acetone dicarboxylic acid, itaconic acid, trimesic acid, limonic acid, keto-limonic acid, pinic acid, and combinations thereof. Mixtures of biocompatible multifunctional carboxylic acids can be used.

Various polyols can be used. Examples of polyols include diols, triols, tetraols, and higher polyols. Non-limiting examples of polyols include macropolyols (e.g., macrodiols) and small molecule polyols such as, for example, aliphatic polyols (e.g., aliphatic diols) and aryl polyols (e.g., aromatic diols). It is desirable that the polyol is biocompatible. Non-limiting examples of polyols include biocompatible polyols. Mixtures of polyols can be used.

A macrodiol is a polymer or oligomer comprising terminal hydroxyl groups. In various examples, a macrodiol is a poly(lactic acid) or another hydrophobic polymer or oligomer functionalized or derivatized to be a diol. In various other examples, a macrodiol is polyethylene glycol (PEG) (e.g., polyethylene glycol having a molecular weight of 100-5,000 g/mol or 200-1,000 g/mol and/or terminal hydroxyl groups), polypropylene glycol (PPG) (e.g., polyethylene glycol having a molecular weight of 100-5,000 g/mol or 200-1,000 g/mol and/or terminal hydroxyl groups).

An aliphatic diol is a saturated or unsaturated aliphatic diol. For example, aliphatic diols are $C_2$ to $C_{30}$ aliphatic diols, including all integer number of carbons and rangers of numbers of carbons therebetween. In an example, an aliphatic diols is a $C_2$ to $C_{12}$ aliphatic diol. Non-limiting examples of aliphatic polyols include branched or linear α,ω-alkane diols or branched or linear α,ω-alkene diols. Aliphatic diols optionally contain degrees of unsaturation. Degrees of unsaturation include, but are not limited to, alkenyl groups/moieties, alkynyl groups/moieties, and cyclic aliphatic groups/moieties. Non-limiting examples of aliphatic diols include ethylene glycol, 1,3-propanediol, 1,4-butanediol, 1,5-pentanediol, 1,3-pentanediol, 1,6-hexanediol, 1,2-hexanediol, 1,5-hexanediol, 2-butene-1,4-diol, and 2-butyn-1,4-diol, 1,8-octanediol, 1,10-decanediol, 1,12-dodecanediol, 1,16-hexadecanediol, 1,20-icosanediol, and combinations thereof.

An aromatic diol may have one or more heteroatoms. Non-limiting examples of diols include 1,6-di-O-benzoyl-D-mannitol, benzenediol, and 1,4-Benzenedimethanol, resorcinol bis(2-hydroxylethyl ether) ether.

Various linker compounds can be used. A linker compound comprises an amine group. In various examples, a linker compound comprises i) an amine group and a carboxylic acid/carboxylate group, ii) amine group and a thiol group, iii) two amine groups. Examples of amine groups include, but are not limited to, an aliphatic amine groups, aryl amine groups, and combinations thereof. Non-limiting examples of linker compounds include amino acids, aminothiols, aryl amines, and combinations thereof. Mixtures of linker compounds can be used.

Various conductive oligomers can be used. A conductive oligomer is conductive and is a pendant group on the oligomeric backbone and/or a terminal group of the oligomer. Non-limiting examples of conductive oligomers include aniline oligomers, pyrrole oligomers, thiophene oligomers, ethylenedioxythiophene oligomers, thiophene (e.g., 3-alkyl thiophene) oligomers, p-phenylenevinylene oligomers, p-phenylenevinylene (e.g., 2,5-dialkoxy p-phenylenevinylene) oligomers, and combinations thereof. Non-limiting examples of aniline oligomers include aniline trimer, aniline tetramer, aniline pentamer, aniline hexamer, and combinations thereof. Mixtures of conductive oligomers can be used.

A compound can have various amounts (e.g., mol %) of conductive oligomers. For example, the conductive oligomer is present at 0.1 to 50 mol %, including all 0.1 mol % values and ranges therebetween, relative to the biocompatible multifunctional carboxylic acid.

In various examples, one or more conductive oligomers are pendant groups linked to the oligomer by an amide linkage between the nitrogen of the conductive oligomer and a pendant carboxylic acid of a biocompatible multifunctional carboxylic acid. In various other examples, one or more conductive oligomers are terminal groups linked to the oligomer by an amide linkage between the nitrogen of the conductive oligomer and a terminal carboxylic acid of a biocompatible multifunctional carboxylic acid or via the carboxylic acid of a linker. In various other examples, one or more conductive oligomers are pendant groups linked to the oligomer by an amide linkage between the nitrogen of the conductive oligomer and a pendant carboxylic acid of a biocompatible multifunctional carboxylic acid and one or more conductive oligomers are terminal groups linked to the oligomer by an amide linkage between the nitrogen of the conductive oligomer and a terminal carboxylic acid of a biocompatible multifunctional carboxylic acid or via the carboxylic acid of a linker.

An oligomer comprises one or more fluorescent cyclic moiety/group (e.g., a fluorescent monocyclic moiety/group or fluorescent bicyclic moiety/group). A fluorescent cyclic moiety/group is covalently bonded as a side group pendent on the oligomer backbone and/or covalently bonded as a moiety within the oligomer backbone, respectively. A fluorescent cyclic moiety/group is formed from the biocompatible multifunctional carboxylic acid and the linker compound.

In an example, a fluorescent cyclic moiety is formed by a carboxylic acid group of an amino acid linker compound, an alpha carbon of the amino acid linker compound, an amide linkage formed by an amino group of the linker, a central carbon of the biocompatible multifunctional carboxylic acid via an esterification reaction of the carboxylic acid group of the linker and the hydroxyl group of the biocompatible multifunctional carboxylic acid.

A compound (e.g., an oligomer) can have various molecular weights. In various examples, a compound (e.g., an oligomer) has a molecular weight of 500 to 10,000 g/mol, including every integer and range therebetween. In various other examples, a compound (e.g., an oligomer) has a molecular weight of 500 to 2,500 g/mol.

In various examples, a compound, oligomer, or precursor oligomer (e.g., a BPLP polymer) has the following structure:

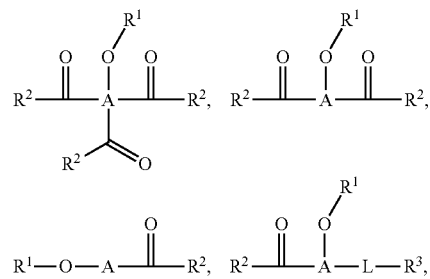

or $R^1$—O-D-O-L-$R^3$,
where A is a an aliphatic group, D is an aliphatic group or an aryl group, L is an aliphatic group, $R^1$ is, independently at each occurrence of the compound, oligomer, or precursor oligomer, i) H; ii) a biocompatible multifunctional carboxylic acid moiety covalently bonded to a conductive oligomer group/moiety, a linker moiety/group, a biocompatible multifunctional carboxylic acid group/moiety, and/or a polyol (e.g., diol) group/moiety and combinations thereof; iii) a linker moiety covalently bonded to a conductive oligomer group/moiety, a linker group/moiety, a biocompatible multifunctional carboxylic acid group/moiety, and/or a polyol (e.g., diol) group/moiety and combinations thereof; iv) a biocompatible multifunctional carboxylic acid group; or v) a linker group. $R^2$ is, independently at each occurrence of the compound, oligomer, or precursor oligomer, i) —OH, ii) a polyol (e.g., diol) group, iii) a conductive oligomer group, iv) polyol (e.g., diol) moiety covalently bonded to biocompatible multifunctional carboxylic acid group/moiety, which is covalently bonded to a conductive oligomer group, a linker group/moiety, a biocompatible multifunctional carboxylic acid group/moiety, and/or polyol (e.g., diol) group/moiety and combinations thereof, v) polyol (e.g., diol) moiety covalently bonded to a linker group/moiety, which is covalently bonded to a conductive oligomer group, a linker group/moiety, a biocompatible multifunctional carboxylic acid group/moiety, and/or polyol (e.g., diol) group/moiety and combinations thereof, or vi) a biocompatible multifunctional carboxylic acid moiety covalently bonded to a conductive oligomer group, a linker group/moiety, a biocompatible multifunctional carboxylic acid group/moiety, and/or polyol (e.g., diol) group/moiety and combinations thereof. $R^3$ is, independently at each occurrence of the compound, oligomer, or precursor oligomer, i) an aliphatic group; ii) an aliphatic moiety further comprising a carboxylic acid group; iii) an aliphatic moiety further comprising an carboxylic acid moiety covalently bonded to a conductive oligomer group, a linker group/moiety, a biocompatible multifunctional carboxylic acid group/moiety, and/or polyol (e.g., diol) group/moiety and combinations thereof; iv) an aryl group; v) an aryl moiety further comprising a carboxylic acid group; vi) an aryl moiety further comprising a conductive oligomer group, a linker group/moiety, a biocompatible multifunctional carboxylic acid group/moiety, and/or polyol (e.g., diol) group/moiety and combinations thereof; or vii) H.

In various examples, a biocompatible multifunctional carboxylic acid group/moiety is covalently bonded to polyol (e.g., diol) group/moiety via an ester linkage at a carbonyl of the biocompatible multifunctional carboxylic acid group/moiety and a terminal oxygen of polyol (e.g., diol) group/moiety. In various examples, a biocompatible multifunctional carboxylic acid group/moiety is covalently bonded to a linker group/moiety via an amine of the linker group/moiety, such that the biocompatible multifunctional carboxylic acid group/moiety condenses with the amine to form a cyclic group/moiety. In various examples, a biocompatible multifunctional carboxylic acid group/moiety is covalently bonded to a conductive oligomer group via an amide linkage at a carbonyl of the biocompatible multifunctional carboxylic acid group/moiety and amine of the conductive oligomer group. In various examples, a biocompatible multifunctional carboxylic acid group/moiety is covalently bonded to a linker group/moiety further comprising a carboxylic acid group via an alcohol of the biocompatible multifunctional carboxylic acid group/moiety and the carboxylic acid of the linker group/moiety.

In various examples, the polyol (e.g., diol) group/moiety is covalently bonded to a biocompatible multifunctional carboxylic acid group/moiety via an ester linkage at a carbonyl of the biocompatible multifunctional carboxylic acid group/moiety and a terminal oxygen of polyol (e.g., diol) group/moiety. In various examples, polyol (e.g., diol) group/moiety is covalently bonded to a linker group/moiety further comprising a carboxylic acid group via an ester linkage at a carbonyl of the linker and a terminal oxygen of the polyol (e.g., diol) group/moiety.

In various examples, the conductive oligomer group is covalently bonded to a biocompatible multifunctional carboxylic acid group/moiety via an amide linkage between an amine group of the conductive oligomer group and a carboxylic acid group of the biocompatible multifunctional carboxylic acid group/moiety.

In various examples, a linker group/moiety is covalently bonded to a biocompatible multifunctional carboxylic acid group/moiety via a condensation reaction at the amine group of the linker group/moiety and at two of the carboxylic acid groups of biocompatible multifunctional carboxylic acid group/moiety to form a cyclic group/moiety. In some examples, the linker group/moiety further comprises a thiol group that further participates in the condensation reaction to for a bicyclic group/moiety. In various examples, a linker group/moiety further comprises a carboxylic acid group. In various examples, a linker group/moiety further comprising a carboxylic acid group is covalently bonded to a polyol (e.g., diol) group/moiety via an ester linkage at the carbonyl of the linker group/moiety and a terminal oxygen of the polyol (e.g., diol) group/moiety. In various examples, a linker group/moiety further comprising a carboxylic acid group is covalently bonded to a biocompatible multifunctional carboxylic acid group/moiety via a condensation reaction at the amine group of the linker group/moiety and at two of the carboxylic acid groups of biocompatible multifunctional carboxylic acid group/moiety to form a cyclic group/moiety. In some examples, the linker group/moiety further comprises a thiol group that further participates in the condensation reaction to for a bicyclic group/moiety.

A polyol (e.g., diol) group/moiety is derived from (formed from) a polyol (e.g., diol) compound. For example, polyol (e.g., diol) group (e.g., 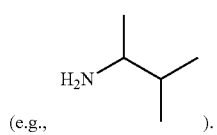)

or a polyol (e.g., diol) moiety (e.g., 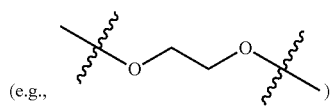)

is derived from a diol compound (e.g., 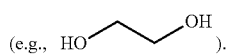).

A biocompatible multifunctional carboxylic acid group/moiety is derived from (formed from) a biocompatible multifunctional carboxylic compound. For example, a biocompatible multifunctional carboxylic acid group (e.g., 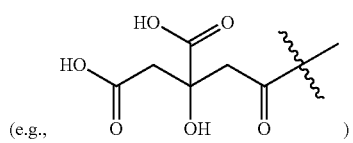)

or and biocompatible multifunctional carboxylic acid moiety (e.g., 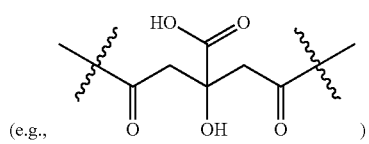)

is derived from a biocompatible multifunctional carboxylic acid compound (e.g., 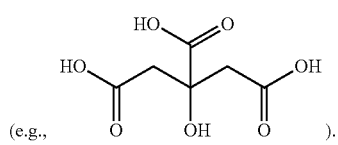).

A linker group/moiety is derived from (formed from) a linker compound. For example, linker groups (e.g. 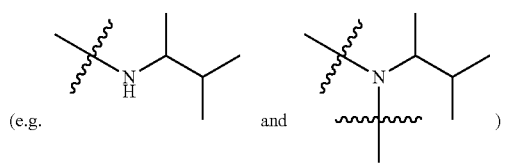)

is derived from a linker compound (e.g., 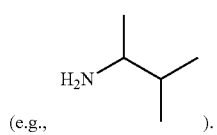).

In another example, a linker moiety

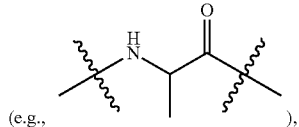

(e.g., ), is derived from the linker compound

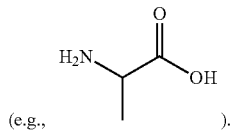

(e.g., ).

In another example, a linker group

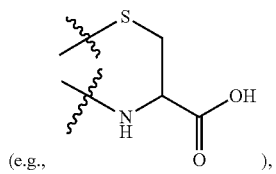

(e.g., ), or a linker moiety

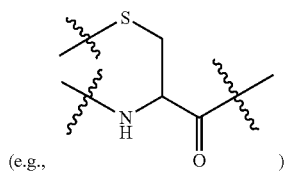

(e.g., ) is derived from a linker compound

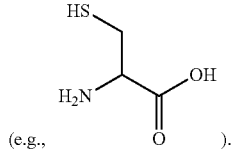

(e.g., ).

A conductive oligomer group is derived from (formed from) a conductive oligomer compound. For example, a conductive oligomer group

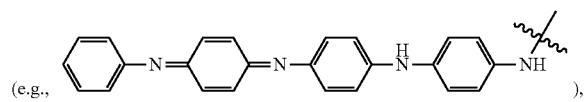

(e.g., ), is derived from a conductive oligomer compound

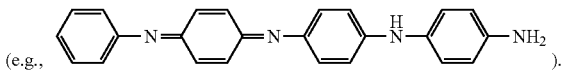

(e.g., ).

A fluorescent cyclic moiety/group is derived from (formed from) a condensation reaction between a biocompatible multifunctional carboxylic acid compound and a linker compound. For example, a fluorescent cyclic group

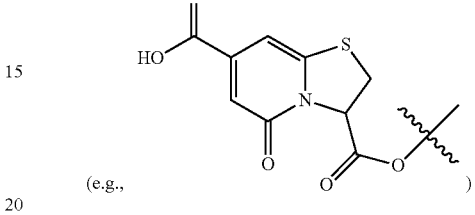

(e.g., )

or a fluorescent cyclic moiety

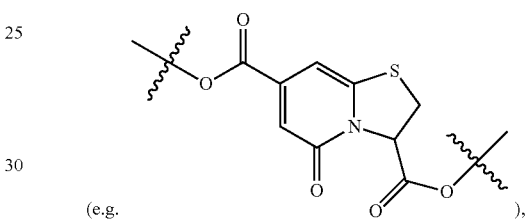

(e.g. ), is derived from a biocompatible multifunctional carboxylic acid compound

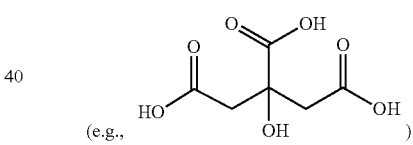

(e.g., )

and a linker compound

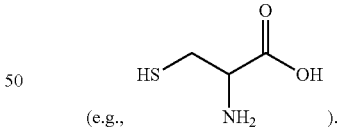

(e.g., ).

In another example, a fluorescent cyclic group

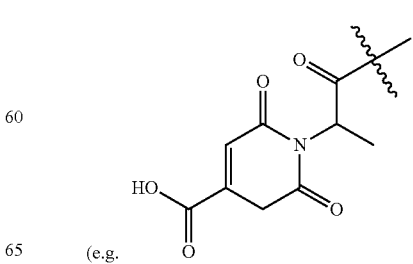

(e.g. )

or a fluorescent cyclic moiety (e.g., 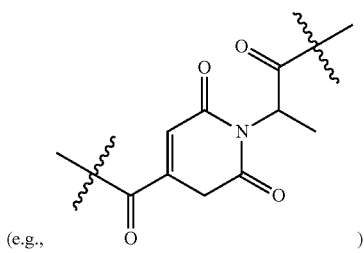)

is derived from a biocompatible multifunctional carboxylic acid compound (e.g., 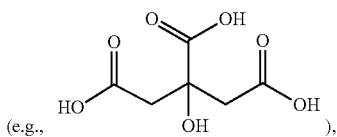), and the linker compound (e.g., 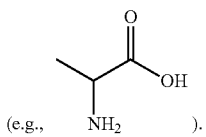).

The compounds can have desirable solubility. For example, the compounds are soluble in dioxane, ethanol, acetone, dimethylformamide, dimethylsulfoxide, and combinations thereof.

The compounds (e.g., pre-polymers) can be crosslinked (e.g., by radical polymerization or thermal treatment (thermally)) to provide elastomeric materials. For example, a composition comprising a plurality of compounds of the present disclosure, which may be the same or different compounds, are thermally treated or subjected to a radical polymerization resulting in a cross-linked elastomeric material. The compounds can be crosslinked by a condensation reaction. The condensation reaction can be a thermal condensation reaction. For example, a compound is thermally crosslinked by heating the compound at 110° C. for three days.

The compounds can be present in various forms. In an example, a film comprises one or more compound of the present disclosure. In another example, a nanoparticle comprises one or more compound of the present disclosure.

In examples, the disclosure comprises compounds (e.g., BPLPATs) comprising pendent carboxyl and/or hydroxyl groups used for surface modification and functionalization to improve cell adhesion, proliferation and targeting. In examples the disclosure includes compounds (e.g., BPL-PATs) conjugated to other agents including but not limited to polymers, proteins, lipids, nucleic acids (e.g., DNA or RNA molecules). In certain examples, the compounds (e.g., BPL-PATs) are immobilized on a surface.

A compound can be conjugated to, for example, a polymer, protein, peptide, lipid, nucleic acid (e.g., DNA), or a surface. In various examples, a compound is conjugated to polymers, proteins (e.g., collagen, serum albumin, VEGF, etc.), peptides (e.g., RGD, R11, etc.), lipids, and nucleic acids, groups metals, ceramics, or surfaces (e.g., with functional groups of, for example, —OH, —COOH, —NH$_2$, or clickable groups). A compound can be conjugated adsorption, conjugation (e.g., carbodiimide chemistry, click chemistry, and the like).

In examples, the disclosure includes compounds (e.g., BPLPATs) for use in promoting nerve cell proliferation and differentiation, including but not limited to use under electrical stimulation, and for use with tissue engineering applications including but not limited to cardiac, blood vessels, skin, bone tissues engineering, etc.

In examples, the compounds (e.g., BPLPATs) can be fabricated into nanoparticles of variable sizes for applications including but not limited to imaging agents and drug carriers. In certain approaches, nanoparticles can be used in labeling cells and biomolecules for both in vitro and in vivo imaging purposes. In various examples, the nanoparticles have a longest dimension (e.g., a diameter) of 20 nm to 1,000 nm (e.g., 150 to 190 nm), including all integer nm values and ranges therebetween. For example, an nanoparticle containing 0.0 mol % (as defined herein) AT has a diameter of 164.3±6.9 nm, a nanoparticle containing 5.0 mol % (as defined herein) AT has a diameter of 178.2±4.3 nm, a nanoparticle containing 10 mol % (as defined herein) AT has a diameter of 182.6±2.0 nm, and a nanoparticle containing 15 mol % (as defined herein) AT has a diameter of 181.9±5.7 nm.

In certain approaches, nanoparticles (e.g., BPLPAT nanoparticles) are used with controllable drug delivery, which can be based at least in part on the electrical chemical properties of the conductive oligomer (e.g., AT) or derivative thereof.

A nanoparticle may further comprise a drug and/or a targeting molecule. Non-limiting examples of drugs include cancer drugs such as, for example, doxorubicin. Non-limiting examples of targeting molecules include peptides such as, for example, RGD motifs, R11, and the like, proteins, antibodies, lipids, nucleic acids (e.g., DNA). A drug and/or targeting molecule can be incorporated by adsorption, conjugation (e.g., carbodiimide chemistry, click chemistry, and the like). A nanoparticle may further comprise functionalities providing targeting, treatment, imaging, sensing, etc. In examples, nanoparticles (e.g., BPLPAT nanoparticles) are modified with specific targeting molecules for targeted drug delivery.

In examples, the compounds (e.g., BPLPATs) can be fabricated into films of variable sizes for applications. In various examples, the films are disposed on a surface, e.g., an implant such as, for example, a biomedical implant, a patch such as, for example, a biomedical patch, and/or drug delivery container. In various examples, the films comprising electroactive elastomers have a thickness of 5 μm to 5 mm (e.g., 100 μm to 1,000 μm). A film may be thermally cured to provide an elastomer film or plastic film. For example, a film is thermally cured at 100° C. for 3 days.

In an aspect, the present disclosure provides methods of making compounds of the present disclosure. The methods can be used to make a compound of the present disclosure. In various examples, a compound is made by a method of the present disclosure.

The methods based on a "one-pot" synthesis where one or more linker compound, one or more biocompatible multifunctional carboxylic acid, one or more polyol (e.g., aliphatic diol), one or more conductive oligomer are combined. In an example, a method of making a compound of the present disclosure comprises: forming a reaction mixture comprising: one or more linker; one or more biocompatible multifunctional carboxylic acid; one or more polyol (e.g., aliphatic diol); one or more conductive oligomer; and heating the reaction mixture (e.g., at temperature of 100 to 160° C.) to produce the compound. Alternatively, the methods are based on reaction of a precursor oligomer (e.g., a BPLP polymer) and one or more conductive oligomer. For example, a method of making a compound of the present disclosure comprises: reacting a precursor oligomer with a conductive oligomer (e.g., at temperature of 100 to 160° C.) to produce the compound. Carbodiimide chemistry or click chemistry may be used to conjugate a conductive oligomer to a precursor oligomer. A method of making a compound of the present disclosure may further comprise isolating the compound from the reaction mixture.

A reaction mixture may further comprise a solvent. Is it desirable that the reactants and or precursor oligomer be at least partially soluble in the solvent. Mixtures of solvents can be used. Non-limiting examples of solvents include dioxane, ethanol, acetone, dimethylformamide, dimethylsulfoxide, and combinations thereof.

In various examples, a reaction mixture that yields a compound of the present disclosure comprises 1.0 equivalent of a biocompatible carboxylic acid, 1.1 equivalents of a polyol (e.g., aliphatic diol), 0.2 equivalents of a linker compound, and 0 to 50 mol % of a conductive oligomer. In other examples, there is an excess (e.g., greater than 1.1 equivalents) of a polyol (e.g., aliphatic diol).

In certain non-limiting examples, the disclosure comprises introducing different amounts of conductive oligomer (e.g., AT) to BPLP systems (e.g., BPLP-cysteine (BPLP-Cys) during the material synthesis processes. BPLP systems (e.g., BPLP-Cys) contribute intrinsically fluorescence, mechanical flexibility, and high solubility in most organic solvents, while the rigid and conductive oligomers (e.g., AT) brings enhanced mechanical properties, cell modulation capability, photothermal performance, as well as deep tissue photoacoustic imaging ability to the obtained compounds (e.g., BPLPATs), as described and demonstrated in this disclosure. As a result, compounds (e.g., BPLPATs) can be fabricated into different constructions (films, scaffolds, and nanoparticles) and used in a broad range of biomedical applications including tissue engineering, cancer therapy, bioimaging, biosensoring, etc.

In certain examples, compositions of this disclosure comprise molar ratios of conductive oligomer (e.g., AT) to biocompatible multifunctional carboxylic acid (e.g., citric acid (CA)) or another biocompatible multifunctional carboxylic acid (e.g., citric acid (CA)) or another biocompatible multifunctional carboxylic acid (mol % of conductive oligomer (e.g., AT) relative to biocompatible multifunctional carboxylic acid (e.g., citric acid (CA)) or another biocompatible multifunctional carboxylic acid) of 0.1-50%, inclusive, and including all numbers there between to the first decimal point. In examples, other biocompatible multifunctional carboxylic acids include but are not limited to citrate, and include but are not necessarily limited to tricarballylic acid, aconitic acid, citraconic acid, acetonedicarboxylic acid, and itaconic acid as substitutes for citric acid. In examples, compositions of this disclosure comprise a molar ratio of conductive oligomer (e.g., AT) to biocompatible multifunctional carboxylic acid (e.g., CA (or a substitute for CA)) of 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 48, 49, or 50 mol %. In examples, a composition of this disclosure comprises a molar ratio of conductive oligomer (e.g., AT) to biocompatible multifunctional carboxylic acid (e.g., CA) of 5%, 10% or 15%. In examples, a composition of this disclosure includes, for example, a one-pot polycondensation reaction wherein the molar ratios of biocompatible multifunctional carboxylic acid (e.g., CA) and conducive oligomer (e.g., AT) with respect to each other are controlled to produce a composition of this disclosure. In examples, use of a combination of precursor oligomer (e.g., BPLP) and conductive oligomer (e.g., AT) during synthesis of the presently provided compounds significantly increase the solubility of conductive materials, such that obtained compounds (e.g., BPLPATs) are able to be dissolved in most organic solvents, including but not limited to dioxane, ethanol, and acetone. In examples, the disclosure includes introducing into a precursor oligomer (e.g., BPLP) system distinct conductive oligomers, including but not limited to aniline oligomers (aniline trimer, aniline tetramer, aniline pentamer, etc.), pyrrole oligomers, and thiophene oligomers, to produce electroactive biodegradable photoluminescent elastomers that are further described below. In examples, compounds (e.g., BPLPATs) of this disclosure are made without using, and do not comprise, any traditional photobleaching fluorescent organic dyes or toxic quantum dots. In examples, compounds (BPLPATs) are not formed by mixing conductive polymers with biodegradable elastomers.

The disclosure includes hydrophobic compounds (e.g., BPLPATs) and amphiphilic compounds (e.g., BPLPATs). In examples, the disclosure comprises use of aliphatic diols (e.g., $C_2$-$C_{30}$ diols) to make hydrophobic compounds (e.g., BPLPATs), and poly(ethylene glycol) (PEG) macrodiols and to replace the aliphatic diols (e.g., $C_2$-$C_{30}$ diols) to make amphiphilic compounds (e.g., BPLPATs).

In approaches that are illustrated by way of the examples and description herein, the disclosure includes tuning the biodegradability, photoluminescent, mechanical properties, and combinations thereof, of compounds (e.g., BPLPATs) by varying types of monomers and/or their feeding ratios.

In examples, the disclosure includes incorporating any one or a combination of linker compounds (e.g., canonical α-amino acids and their derivatives, any amine-containing molecules comprised by the fluorophore structure in compounds (e.g., BPLPATs), including but not limited to including distinct amino acids such that the compounds (e.g., BPLPATs) emit light in various regions of the visible spectrum up to near infrared when excited at various wavelengths.)

In an aspect, the present disclosure provides uses of compounds of the present disclosure. For example, an article of manufacture comprises one or more compound or crosslinked compound of the present disclosure. In various examples, the present disclosure provides methods of using the compounds of the present disclosure.

In examples the disclosure includes articles of manufacture that can be used in the imaging approaches described herein. In examples the article of manufacture comprises or consists of a compound (e.g., BPLPAT) or a crosslinked compound. There is no particular limitation to the article of manufacture, other than that it can be used in a process that involves at least generation of a photoacoustic signal from the compound (e.g., BPLPAT). In examples, the compounds (e.g., BPLPATs) are used to make articles by extrusion, electrospinning, coating onto a surface, molding, or being formed into any of a film, fiber, ribbon or tube. In examples, the compounds (e.g., BPLPATs) are used to make nano-scale objects such as nanotube arrays. In examples, the compounds (e.g., BPLPATs) are coated onto the surface of any object, for example, nanoparticles. As noted above, in examples, particles coated with, comprising, or formed of the compounds (e.g., BPLPATs) can be conjugated to a biological molecule that can, for example, target the cell to a particular location or cell type. In examples, the compounds (e.g., BPLPATs) are conjugated to an agent that is at least one of an antibody and/or an antigen binding fragment thereof including single-chain antibody fragments and Fabs, a receptor ligand, a growth factor, a cytokine, a toxin, an enzyme, a transcriptional factor, a growth factor, peptide or protein immunogens, a chemotherapeutic agent including but not limited, protein-based chemotherapeutic agents. In examples, the compounds (e.g., BPLPATs) can be conjugated to a component of a macromolecule, such as a peptide or protein, wherein the macromolecule has a cellular localization function, including but not necessarily limited to a signal for extracellular transport, i.e., secretion, or for nuclear import. Thus, in examples, compounds (e.g., BPLPATs) can be used to assess the function of any of a variety of drugs. In examples, the compounds (e.g., BPLPATs) can be conjugated to a detectable label, including but not necessarily limited to a radiolabel, or a fluorescent label that is, for example, separately detectable relative to fluorescence produced by the compound (e.g., BPLPAT).

Nanoparticles of this disclosure that are coated and/or impregnated with one or more compound of the present disclosure (e.g., BPLPATs) can be formed of any suitable material, such as any suitable biocompatible material, including but not limited to glass, silicate, and biocompatible polymers. In various examples, one or more compound of the present disclosure (e.g., BPLPATs) can be integrated into a hydrogel. In various examples, one or more compound of the present disclosure (e.g., BPLPATs) are comprised within a biocompatible scaffold, such as for tissue generation, regeneration and/or repair.

Compounds of the present disclosure can be used in imaging methods. The imaging methods can be photoacoustic imaging methods, fluorescence imaging methods, or a combination thereof.

In an example, a photoacoustic imaging method (e.g., a method of generating an image of an animate human or non-human animal body or part thereof) comprises exposing the body or part thereof (e.g, that includes a compound or elastomer of the present disclosure) to electromagnetic radiation and detecting pressure waves generated (e.g., an acoustic signal) in the body by the electromagnetic radiation and generating an optoacoustic image therefrom of at least a part of said body containing the compound or elastomer.

In an example, a method for generating an acoustic signal comprises: subjecting a compound of the present disclosure, which may be present in a human or non-human mammal body or a part thereof, to a stimulus comprising electromagnetic radiation (e.g., provided by a laser such as, for example, a pulsed laser, having (e.g., comprising) a wavelength of 280-1000 nm (e.g., 360-920 nm or 680-920 nm), where an acoustic signal (e.g., a photoacoustic signal) is generated (e.g., generated in vivo or in vitro). The method may further comprise detecting the acoustic signal. The method may further comprise generating an image from the acoustic signal. In the method, the subjecting the compound to electromagnetic radiation also generates (or a different electromagnetic radiation generates) a fluorescence signal and the method may further comprises detecting the fluorescence signal. The method may further comprise generating an image from the fluorescence signal.

Various images can be generated. An image can be a 2-D or 3-D image. In various example, an image is a photoacoustic image (e.g. a 2-D or 3-D photoacoustic image), a fluorescent image (e.g. a 2-D or 3-D fluorescent image), an ultrasound image (e.g. a 2-D or 3-D ultrasound image), or a combination thereof (e.g., composite image).

In examples, the disclosure comprises photoacoustic imaging of a substance that comprises, consists of, or is in contact (i.e., is fully or partially coated) with a composition of this disclosure, and can optionally further include fluorescence imaging and/or ultrasound imaging. Thus, aspects of this disclosure provide compositions that are able to produce a fluorescent signal, and further take advantage of a photoacoustic effect to provide for novel imaging compositions and approaches. In this regard, and as is known in the art, a photoacoustic effect generally comprises formation of sound waves following light absorption by a material. To produce a photoacoustic signal, a stimulus is applied to a polymer described herein, which leads to emission of sound waves. Many devices that are used for generating and detecting photoacoustic signals are known in the art and can be adapted for use with the compositions of this disclosure.

In certain and non-limiting examples, the stimulus used to produce a photoacoustic effect (i.e., a photoacoustic signal, also referred to as an acoustic signal) comprises a light source; any suitable light source can be used. In examples, the light has a wavelength range of visible light, near infrared light, or mid-infrared light. In examples, a light source having comprising a wavelength of 280-1000 nm (e.g., 360-920 nm or 680-920 nm) is used. In examples, a non-ionizing radiation (NIR) laser is used as a light source. In a non-limiting implementation, an 808-nm NIR laser can be used. In a non-limiting implementation, an 680-nm laser can be used. In examples, ultrashort laser pulse (e.g. 1~10 ns) are used, for example, to improve conversion efficiency from light absorption to ultrasound emission. In examples, the light used to generate photoacoustic measurements is guided by an optical fiber.

In examples, a laser configured to illuminate a material is adapted to be a component of a device that can be used to image cells, tissues, organs, and organisms. In examples, a light source such as a laser configured to illuminate a material is a component of an endoscope.

In examples, non-ionizing laser pulses or another suitable light source are used such that energy is absorbed by the polymer, creating a thermoelastic expansion of it and an emission of sound waves, such as a wide band emission, or an ultrasonic emission, which is thus a type of a photoacoustic signal. In this regard, a photoacoustic signal refers to a sound wave produced by one of several processes, methods, interactions, or the like (including light absorption) that provides a signal that can then be detected and quantitated with regards to its frequency and/or amplitude. The magnitude or other parameters of the photoacoustic signal can be measured using any suitable techniques and/or devices, and reveals a physiological specific absorption contrast which can be used to form two-dimensional or three-dimensional images. Thus, in examples, the disclosure pertains to use of the polymers described herein for photoacoustic imaging, i.e., for use in generating and detecting an acoustic signal by exposing a polymer of this disclosure to a light source, wherein the polymer absorbs the light and converts absorbed energy into thermal energy that causes generation of an acoustic signal through a process of thermal expansion, and wherein the acoustic signal is converted into an image. In general, the acoustic signal is detectable and distinguishable from other background acoustic signals that are generated from the subject or sample. Thus, there is a measurable and statistically significant difference to distinguish among the acoustic detectable signal and the background. In examples, there is about 0.1%, 1%, 3%, 5%, 10%, 15%, 20%, 25%, 30%, or 40% or more difference between the acoustic detectable signal and the background. In examples, an acoustic signal may comprise a sum of separate individual photoacoustic signals. In an example, the acoustic signal can be generated from a summation, an integration, or other mathematical process, formula, or algorithm. In examples, the acoustic signal is from one or more probes.

Standards and/or calibration curves can be used to determine the relative intensity of the acoustic detectable signal and/or the background, and comparisons of the photoacoustic signals produced by the compositions of this disclosure can be compared to any suitable control. For example, a PA signal generated by a composition of this disclosure is compared to a BPLP control, or to a BPLPAT control with a lower amount of AT than an experimental BPLPAT, wherein the experimental BPLPAT produces a greater PA signal than the control.

The acoustic detectable signal can be detected using any suitable approaches, devices, systems, etc. In examples, the photoacoustic signal is detected in a photoacoustic cell which may be comprised of acoustic resonators, buffers, filters, etc.

In examples, the disclosure includes systems for photoacoustic imaging, which may be combined with fluorescence imaging, and/or with ultrasound imaging. In examples, a PA system includes a photoacoustic probe comprising a light irradiation unit that irradiates light to a subject and a transducer that receives an acoustic signal, such as an ultrasound signal, generated from the subject and converts the acoustic signal into a different signal, such as an electric signal. In examples, the system comprises a signal processor that processes a photoacoustic signal of the photoacoustic wave detected by the acoustic wave transducer. In examples, the system can include one or more microphones, and/or devices suitable for piezoelectric detection. In examples, the system can comprise acoustic resonators. In examples, the system can include one or more computers and/or processors configured to run software that converts the acoustic signal into an image. In examples, the disclosure includes use of the compositions described herein for 3D photoacoustic microscopy (PAM). In examples the disclosure includes phase matching or reflected acoustic waves and photoacoustic signals.

In examples the disclosure comprises generating a 2D or 3D image that is comprised of data from photoacoustic imaging alone, or a combination of photoacoustic imaging with fluorescence imaging, and/or ultrasound imaging. In examples, the disclosure includes fixing the image in a tangible medium of expression, such as an electronic file, and may further comprising communicating the tangible medium of expression to a third party, one non-limiting example of which may be a health care provider, including but not necessarily limited to a pathologist, oncologist, and/or a radiologist.

The disclosure includes consecutive imaging, such as for the monitoring (e.g., without sacrificing an animal) the status (i.e., degradation, stability, etc.) of a biocompatible implant that comprises and/or is formed of one or more compound of the present disclosure (e.g., BPLPATs). Thus, methods for monitoring using in vivo approaches are included.

The steps of the methods described in the various embodiments and examples disclosed herein are sufficient to carry out the methods of the present disclosure. Thus, in an example, a method consists essentially of a combination of the steps of the methods disclosed herein. In another example, a method consists of such steps.

The following examples are intended to illustrate, but not limit, the present disclosure:

EXAMPLE

This example provides a non-limiting example of synthesis, properties and uses of BPLPATs.

Materials and methods. Materials. All chemicals were purchased from Sigma-Aldrich, and were used as received without further purification, except where mentioned otherwise.

Synthesis of aniline tetramer (AT). The synthesis of aniline tetramer (AT) was carried out by following the procedure. In brief, N-phenyl-1,4-phenylenediamine (3.6848 g, 0.02 mol) was dissolved in a mixture of acetone and 1 mol/L HCl (V/V 160:160 mL) at 0° C. in an ice bath. Ammonium persulfate (APS) (4.564 g, 0.02 mol) in acetone/HCl solution was then added drop by drop to the above solution during 30 min with vigorous stirring. The reaction was conducted in air for 2 hrs. The mixture was filtered to collect the AT, and the cake was then washed with 1 mol/L HCl and distilled water. The AT was dedoped in 1 mol/L $NH_4OH$ for 2 hrs and was filtered and washed until the filtrate was neutral. Finally, the AT was freeze dried for 24 hrs.

Synthesis of BPLPATs. BPLPAT pre-polymers were synthesized using a one-pot polycondensation reaction as illustrated in the synthesis schematic (FIG. 1a). In brief, citric acid (CA), 1,8-octanediol (OD), L-cysteine, and AT with strict molar ratios were added to a round-bottom flask, and the reaction was carried out at 110° C. under nitrogen atmosphere for ~5 hrs until the stir bar was twitched at 80 rpm. The pre-polymer was dissolved by 1,4-dioxane and purified by precipitating the solution into distilled water. Finally, BPLPAT pre-polymers were freeze dried for 24 hrs for future use. The theoretical molar ratios of AT to CA were set as 5%, 10% and 15%, respectively. Obtained polymers were named as BPLP, BPLPAT5%, BPLPAT10%, and BPLPAT15%, respectively.

Preparation of BPLPAT films, nanoparticles, and scaffolds. BPLPAT films were prepared by casting their dioxane solution into Teflon molds and followed by evaporation and heat crosslinking at 100° C. for 3 days. In this process, part of the un-reacted —COOH and —OH groups of BPLPAT prepolymers were cross-linked. For nanoparticle preparation, 0.4 g of BPLPAT was dissolved in acetone (10 mL). The polymer solution was added dropwisely to deionized water (20 mL) under magnetic stirring (600 rpm). The setup was left in chemical hood for 6 h in chemical hood to evaporate acetone. Desired concentration of nanoparticle solution can be achieved by evaporating water and dilution. Polymer scaffolds were prepared by the traditional salt leaching method.

Characterization. Attenuated total reflectance-Fourier transform infrared (ATR-FTIR) characterization was performed on a Bruker Vertex 70 FTIR spectrometer with a Pike Miracle Single-Bounce diamond crystal plate accessory at room temperature. FTIR spectra were recorded over a wavelength range of 4000-500 $cm^1$. Nuclear magnetic resonance ($^1$H-NMR) spectra in DMSO-$d_6$ were recorded on a 300 MHz Bruker DPX-300 FT-NMR spectrometer. All photoluminescence spectra were acquired on HORIBA Scientific Fluoromax-4 spectrofluorometer. All pre-polymers were dissolved in 1,4-dioxane to test photoluminescence unless otherwise noted. Both the excitation and the emission slit widths were set at 2 nm. The UV-vis spectra of BPLPAT prepolymers and their CSA-doped and APS-doped solutions were recorded with a UV-2450 spectrophotometer. Absorption spectra from 280 nm to 1000 nm were recorded. All the sample was dissolved in DMSO with the same concentration and the sample solution was doped with 1 mol/L CSA and APS. The cyclic voltammetry (CV) was performed with an Autolab PGSTAT-302N in a conventional three-electrode system with a platinum wire as working electrode, a platinum foil as auxiliary electrode, and an Ag/AgCl as reference electrode. Polymer solutions in ethanol were applied for the test, and 1 mol/L CSA was used for material doping. The scan rate was 50 mV/sec for all the samples.

Mechanical properties. Mechanical testing was conducted according to the ASTM D412a standard on an Instron 5966 machine. For tensile testing, the Instron machine was equipped with a 500 N load cell. Polymer film samples (3 cm in length, 0.6 cm in width, and 200 µm in thickness) under both dry and hydrated (immersed in PBS for 24 hr) conditions were applied for the testing. Samples were pulled until failure at a rate of 500 mm/min to obtain the stress-strain curves. The initial slope (0-10%) of the curve was used to determine the initial modulus of the samples. Compression testing was applied on polymer scaffold samples (7 mm in diameter, and 3 mm in thickness). Samples were compressed until reach 50% of the thickness at a rate of 1.3 mm/min with a 1 kN load cell. Six specimens were averaged for each sample, and the results are presented as means±standard deviation.

Electrical conductivity measurements. A four-point probe (Jandel Engineering Ltd.) was used to measure the electrical conductivity of BPLPAT film (doped with CSA) at room temperature. The conductivity was calculated by the following formula: $R_b=4.532(V/I)t$, where $R_b$=Bulk resistivity, V=measured voltage, I=current setting, and t=thickness of layer being measured in cm. The electrical conductivity was then calculated using the following equation: $\sigma=1/R_b$.

In vitro degradation studies of BPLPAT prepolymers and films. In vitro degradation was conducted with ~80 mg of BPLP and BPLPAT10% pre-polymers, as well as BPLP and BPLPAT10% films (with thickness around 0.15-0.30 mm) placed in tubes containing 10 mL of phosphate buffered saline (PBS, pH=7.4) and incubated at 37° C. The samples were weighed to find the initial mass ($W_0$). For prepolymer degradation, PBS buffer was replaced daily to ensure a constant pH of 7.4. For crosslinked film samples, PBS buffer was replaced daily in the first week and weekly in subsequent. At each desired time point, the samples were taken out and thoroughly washed with deionized water 3 times, and then lyophilized. Each sample was weighed to find the remaining mass ($W_t$). Six parallel specimens were averaged, and the results are presented as means±standard deviation. The percent mass remaining was calculated based on the following equation:

$$\text{Mass Remaining (\%)} = \frac{W_t}{W_0} \times 100\% \quad (1)$$

In vitro cytotoxicity studies on BPLPAT films. *Degradation cytotoxicity*: The relative cytotoxicity of degradation products were quantitatively assessed by Cell Counting Kit-8 (CCK-8) assay against PC-12 Adh cells (ATCC® CRL-1721.1™). PLLA was used as a control. Polymer films (1 g) were fully degraded in 10 mL of 2 M NaOH solution. The resultant degradation products solutions were adjusted to pH 7.4 with 1 M HCl solution and then diluted to 1:1, 1:10, and 1:100 concentrations using PBS (pH 7.4). All the solutions were filtered through a sterilized 0.22 µm filter prior to cell culturing. PC12 cells were cultured in a surface treated 25 cm² tissue culture flasks with F-12K medium (Kaighn's Modification of Ham's F-12 Medium (ATCC® 30-2004™) supplemented with 2.5% fetal bovine serum (FBS), 15% horse serum and 1% antibiotics. The cells were detached and suspended in media to obtain a seeding density of $5\times10^4$ cell/mL. 200 µL of the suspension was added into 96 well plates. The cells were then incubated at 37° C., 5% $CO_2$ and 95% humidity for 24 hours. 20 µL of diluted degradation solution was added to each well. After another 24 hours culturing, CCK-8 was applied to test cell viability. The cell viabilities of PC12 cells in medium containing polymer degradation solutions were normalized to that of cells cultured in normal medium. Cell proliferation study: To test the cytotoxicity of polymer films, PLLA was used as a control. Films were cut in round shape to fit 96-well plates. The films were sterilized by treating with 70% ethanol, UV light, and culture medium in sequence. 200 µL of the cell suspension in culturing media with the density of $1\times10^4$ cells/mL was added to each well in a 96-well plate with a film sample on the bottom. CCK-8 was applied to test cell viability at time points of 1, 3, 5, and 7 days to study PC12 proliferation.

Electrical stimulation of PC-12 Adh cells on BPLPAT films and scaffolds. A homemade electrical stimulation device was used for electrical stimulation study on PC12 Adh cells. Cells were seeded at a density of $3\times10^4$ cells/mL in cell differentiation culture media (F-12K medium supplemented with 1% horse serum, 1% antibiotics and 50 ng/mL nerve growth factor (NGF)) on BPLP, BPLPAT5%, BPLPAT10%, and BPLPAT15% films (2 cm×2 cm), and allowed to adhere for 24 hr. A 100 mV/mm potential was then applied for 2 hr, and the cells were cultured for another 24 hr. Then films fixed with 2.5% glutaraldehyde were used for scanning electron microscopy (SEM) study. Experimental processes conducted on BPLPAT scaffolds were the same as that of BPLPAT films, except a higher density of cells ($1\times10^6$ cells/mL).

Cell uptake and fluorescence labeling. The cell uptake of the fluorescent nanoparticles was also examined in vitro. 1 mL PC12 cell suspension was added into each well of 24-well plates with a cell density of 5,000 cells/mL. Cells were allowed to attach and grow for 24 hours before uptake studies were performed. Then the media was aspirated and the cells were washed three times with PBS. After 4 hours of incubation with BPLPAT nanoparticles (10 mg/mL in PBS), the nanoparticle suspension was aspirated and the cells were washed three times with PBS to remove the excess nanoparticles, which had not been uptaken. The cells were fixed with 4% paraformaldehyde for 2 hours. After fixing, cells were mounted and imaged under a Leica DMLP fluorescence microscope (Leica Microsystems, Bannockbum, Ill.) equipped with a Nikion E500 Camera (8.4V, 0.9 A, Nikon Corp., Japan).

Results and Discussion. Synthesis of BPLPAT Prepolymers BPLPAT prepolymers were synthesized by the polycondensation reaction of citric acid, 1,8-octanediol, L-cysteine, and AT (FIG. 1a). According to the theoretical molar ratios of AT in polymer chains, which set as 0 wt %, 5 wt %, 10 wt % and 15 wt %, the samples were named as BPLP, BPLPAT5%, BPLPAT10%, and BPLPAT15%, respectively. In ATR-FTIR spectra (FIG. 1b), the absorption peaks at 1527 cm⁻¹ (—C(=O)NH—), 1713 cm⁻¹ (—C(=O)OR), 2576 cm⁻¹ (—SH), 2932 cm⁻¹ (—$CH_2$—), 3467 cm⁻¹

(—OH) are from BPLP-Cys. The two peaks at 1488 and 1568 cm$^{-1}$ in the spectra of BPLPATs are assigned to the vibration of the quinoid ring and benzene ring in AT. In $^1$H-NMR spectra of BPLPATs (FIG. 1c), peaks at 1.23 ppm and 1.50 ppm represent —CH$_2$— from 1,8-octanediol, and the multiple peaks at 2.75 ppm represent —CH$_2$— from citric acid. Two small peaks at 5.85 and 6.57 ppm were attributed to —(C=CH$_2$)— from cysteine. Peaks at 6.88, 7.00, 7.26, and 7.50 ppm illustrate the 17 Hs in the benzene ring of AT, and the peak at 7.85 ppm came from $^1$H in the secondary amine of AT. Both ATR-FTIR and $^1$H-NMR results confirmed the successful synthesis of BPLPAT prepolymers.

Figure 2:
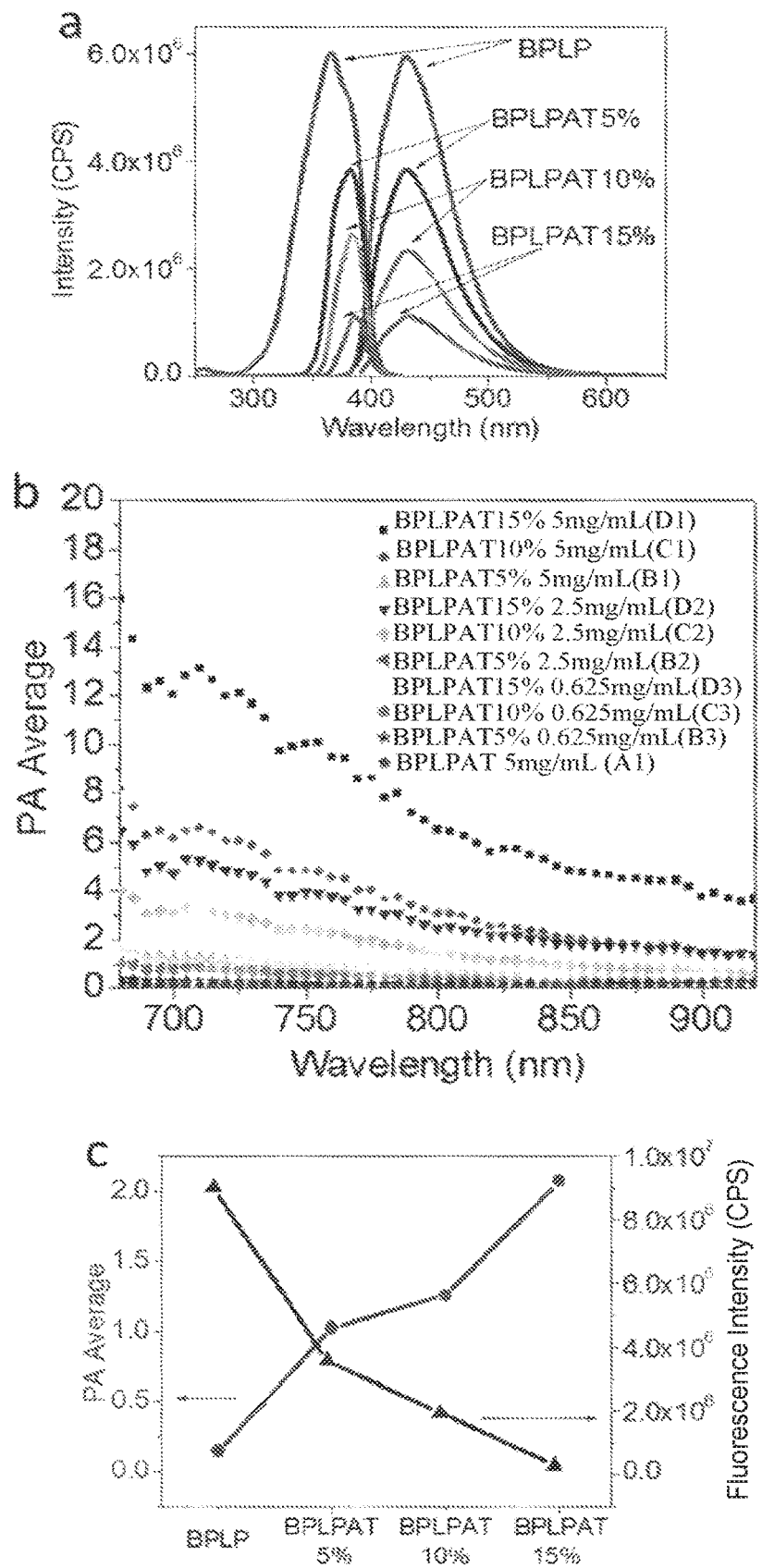
FIG. 2 shows fluorescence and PA properties of BPLPAT prepolymer solutions. (a) Fluorescence intensity spectra of BPLPAT prepolymers in dioxane at 1.25 mg/mL. (b) PA intensity of BPLPAT prepolymers in dioxane at various concentrations. (c) PA intensity and fluorescence intensity comparison of BPLPAT solutions at 2.5 mg/mL (data shown from top to bottom corresponds directly with the legend from top to bottom). (d) Representative overlaid ultrasound and PA images of BPLPAT prepolymer solutions at various concentrations.
Figure 2:
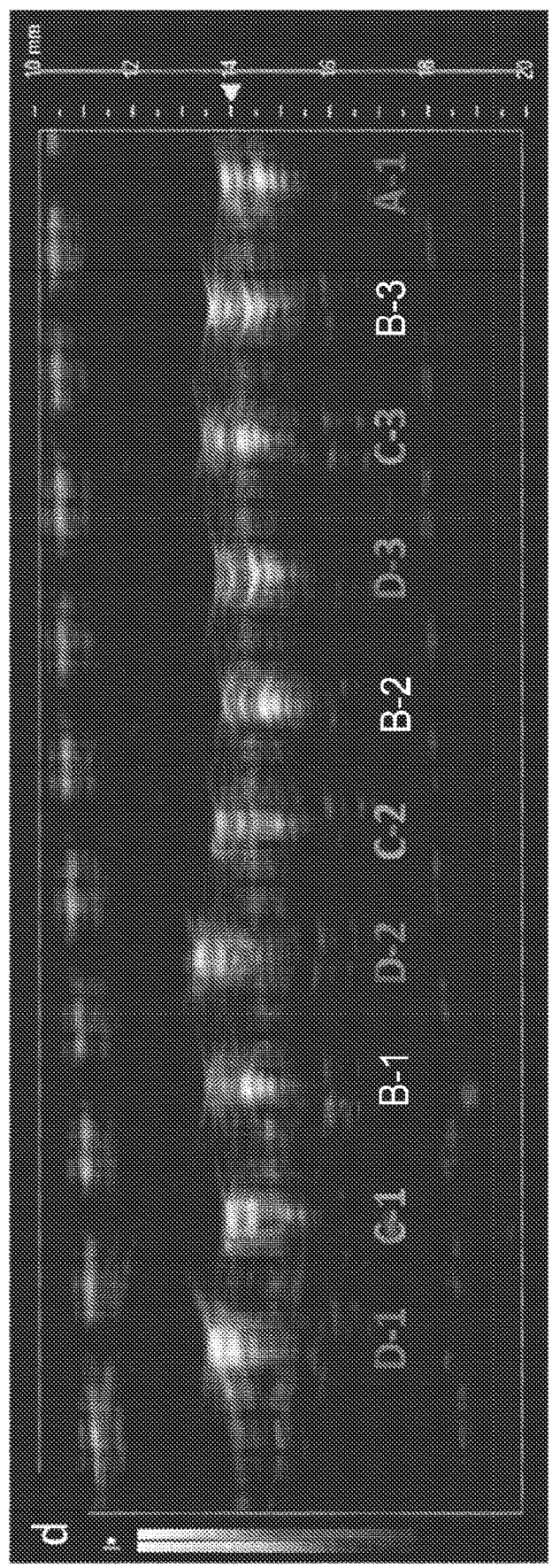
Figure 7:
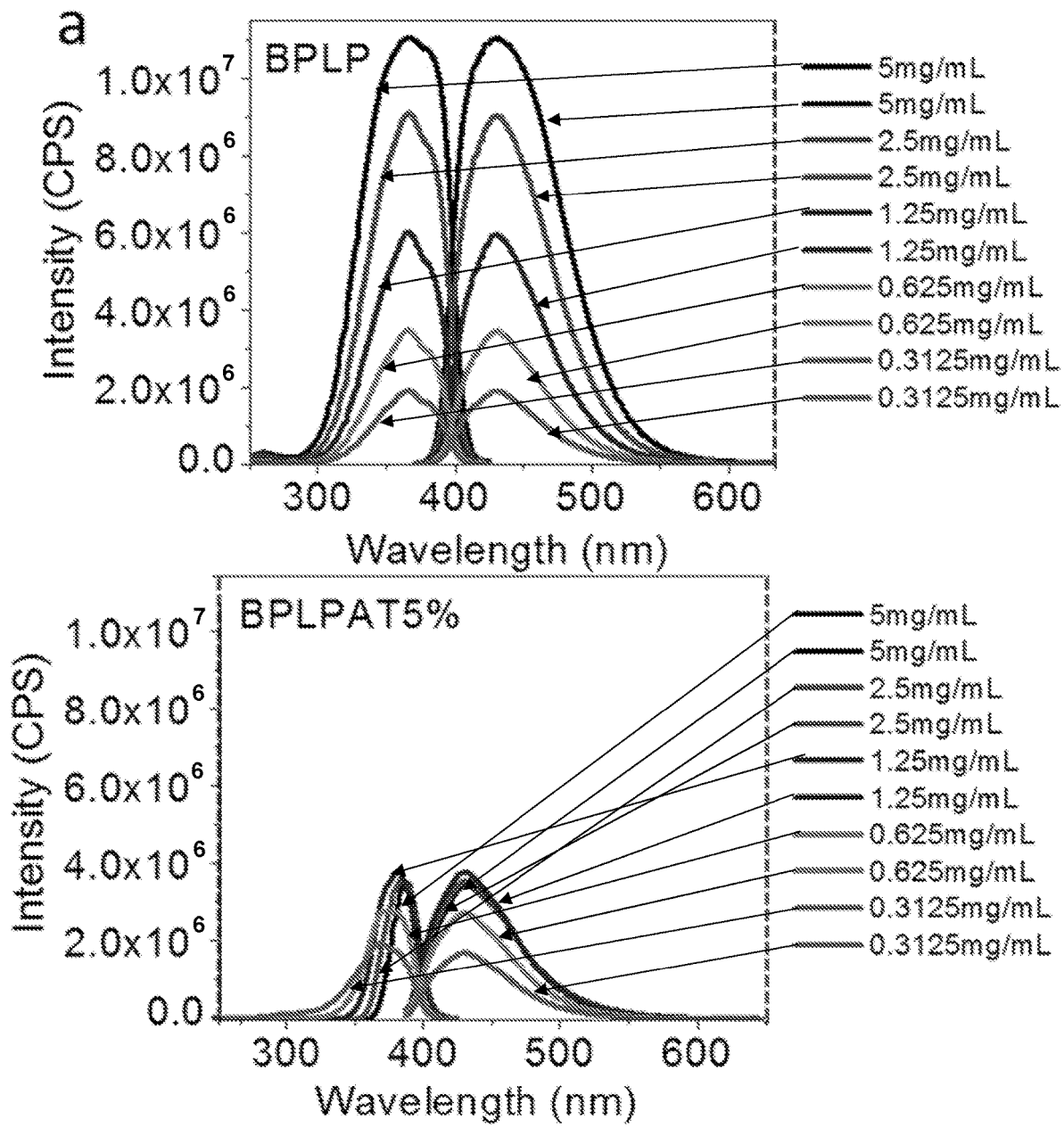
FIG. 7 shows fluorescent properties of BPLPAT prepolymers. (a) Fluorescent intensity testing of BPLP and BPLPAT solutions at various concentrations. (b) Emission peak of BPLP and BPLPAT solutions at various concentrations. (c) Photostability of BPLP and BPLPAT solutions.
Figure 7:
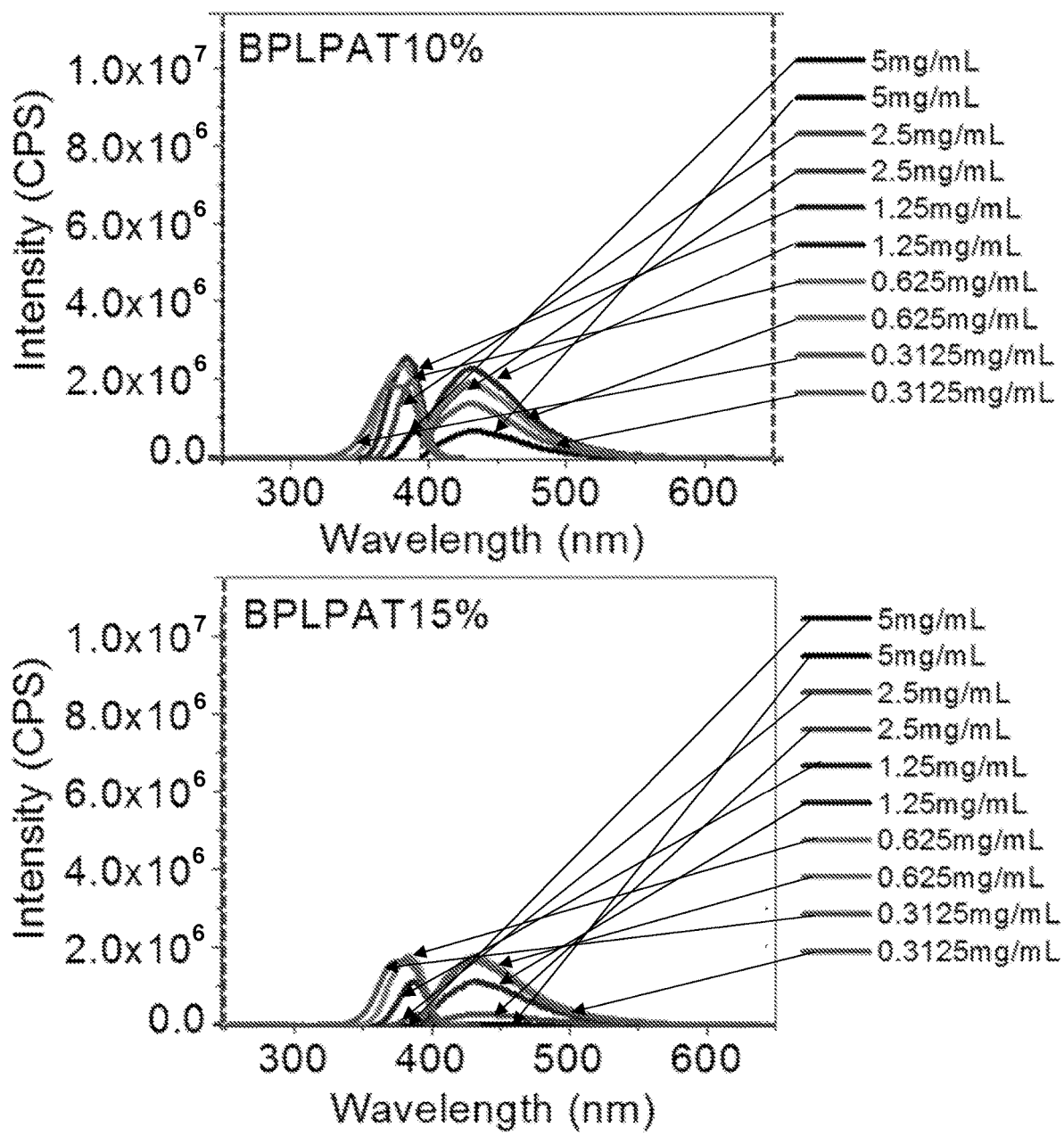
Figure 7:
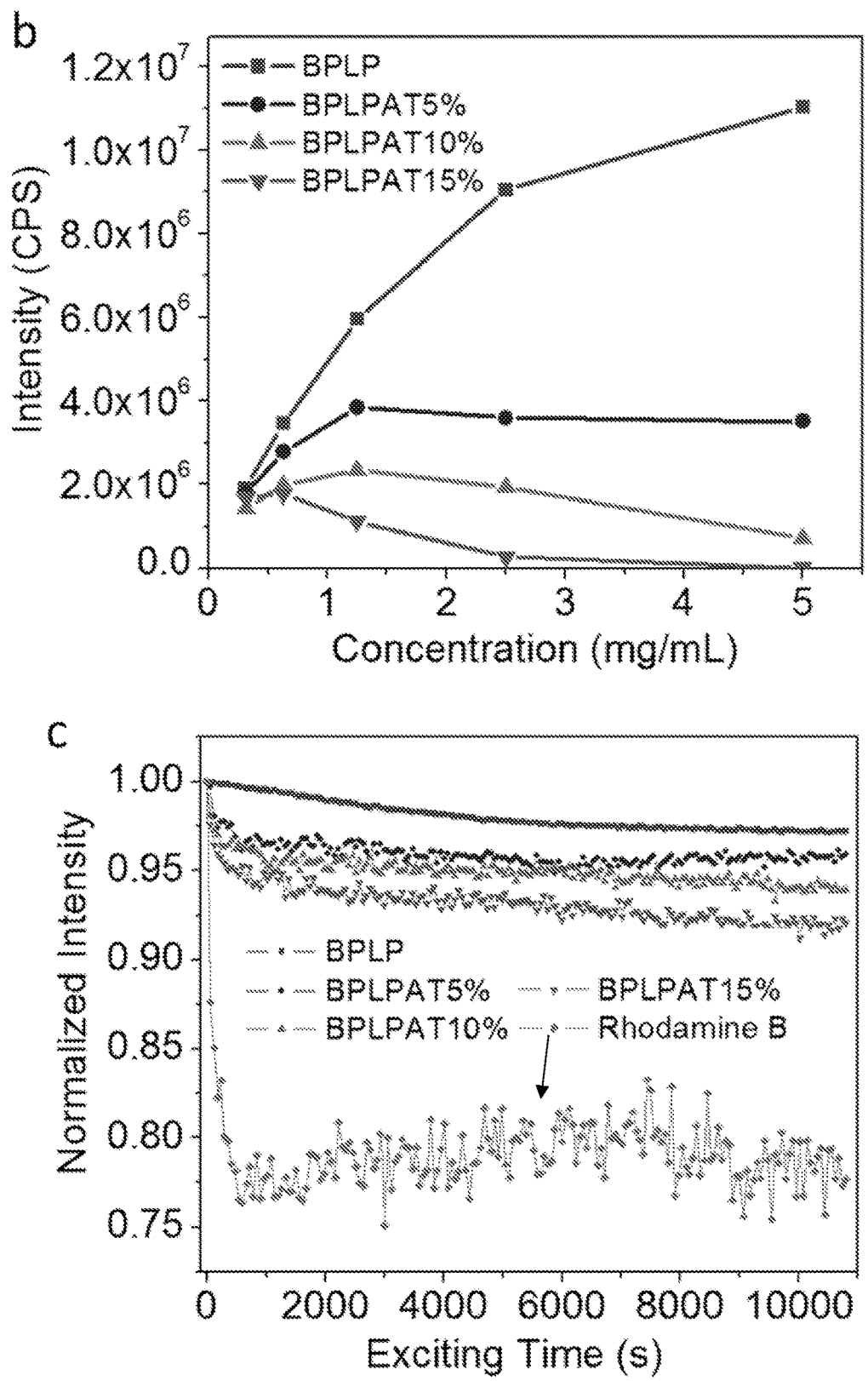

Photoluminescent and Photoacoustic Properties. The fluorescence intensity of BPLPAT prepolymer solutions at different concentrations (5, 2.5, 1.25, 0.625, and 0.3125 mg/mL) were tested (FIG. 7a). Due to the dark color introduced by AT, the fluorescence intensity of BPLPATs were generally lower than BPLP, and also decreased with increased proportion of AT at the same concentration. For comparison, the excitation and emission spectra of BPLP and BPLPAT solutions at the concentration of 1.25 mg/mL are presented in FIG. 2a. BPLP solution had a maximum excitation at around 360 nm and a maximum emission at about 431 nm, while BPLPAT solutions showed a maximum excitation at around 380 nm and a maximum emission at 431 nm, which means BPLPAT solutions have narrower Stokes shifts than BPLP solutions. It is notable that the maximum emission of BPLPAT solutions showed an intensity peak under the testing concentration range, rather than that of BPLP solution had stronger intensity with the increasing of concentrations (FIG. 7b). After continuous ultraviolet (UV) light illumination for 3 hr, BPLPATs presented excellent photostability when compared with the commercial organic fluorescent dye rhodamine-B, although they were slightly less stable than BPLP. The photoacoustic (PA) imaging performance of BPLPATs were also investigated under variable wavelength (680-920 nm). The quantitative comparison of the PA signal intensities of BPLPAT solutions at different concentrations are shown in FIG. 2b. BPLP solution at a high concentration of 5 mg/mL presents no significant PA signal. However, due to strong absorption of light under the testing wavelengths, BPLPATs present distinct PA signals that increased with the ratio of AT (BPLPAT15%>BPLPAT10%>BPLPAT5%), and the intensity also goes up with the concentration of polymer solutions at each group of BPLPATs. The PA imaging performance of BPLPAT solutions is also confirmed by the representative overlaid ultrasound and PA images of each samples at 680 nm in FIG. 2d. To understand the imaging properties of BPLPATs, the emission peaks and PA intensities of BPLPAT solutions at the same concentration of 2.5 mg/mL were studied. As indicated in FIG. 2c, the fluorescence intensity decreases with the ratio of AT, while the PA imaging performance increases significantly. Thus, the introduction of AT to BPLP lessens the photoluminescence properties (intensity, Stokes shift, and photostability), but it also demonstrates the capacity for PA imaging by addition of AT.

Electrochemical Properties and In vitro Degradation Properties. Electrochemical properties of materials were characterized by an Autolab PGSTAT-302N and a UV-2450 spectrometer. In cyclic voltammogram (CV) study (FIG. 3a), all BPLPAT groups (BPLPAT5%, BPLPAT10%, and BPLPAT15%) presented oxidation and reduction transition peaks due to the structure of AT. The CV curves of BPLPATs exhibited two oxidation/reduction peaks at around 0.38 and 0.69 V, which correspond to AT's structure transition from the leucoemeraldine base state to the emeraldine state, and from the emeraldine state to the pernigraniline state. The UV absorption spectra of AT and BPLPAT10% presented two peaks at around 320 and 590 nm, which are assigned to the π-π* transition of the benzenoid ring and the excitonic transition from the benzenoid ring to the quinonoid ring, respectively. After doping AT and BPLPAT10% solutions with CSA, two new absorption peaks at about 430 and 800 nm together with a slight blue shift of the benzenoid absorption peak to 308 nm appeared in their spectra due to the formation of delocalized polarons, which indicated the generation of conductive phase of emeraldine salts (EMS) (FIG. 3b). The results from CV curves and UV spectra confirmed the favorable electrochemical properties of BPLPATs. The conductivities of the BPLPAT films doped with CSA were increased from 1.06×10$^{-7}$ to 2.94×10$^{-6}$ S/cm with the increasing of AT content (Table 1), which are relatively low but are sufficient for the signal transformation and chemical exchange between cells in life activities. Biodegradable polymers serve as biomedical implants or devices leave no long-term concerns, since they can be absorbed or removed through the living system. Due to the introduction of AT, it is important to analyze the degradation performance of these new materials. In vitro degradation studies were conducted on BPLP and BPLPAT10% pre-polymers (FIG. 3c), as well as their crosslinked films (FIG. 3d). Before crosslinking, BPLP and BPLPAT10% pre-polymers showed similar degradation rates (~16 days) (FIG. 3c). While after crosslinking, BPLPAT10% film degraded much slower than BPLP film. As indicated in FIG. 3d, BPLP film could completely degraded within about 18 weeks, at which time BPLPAT10% film still had around 50% mass remaining. The introduction of AT is able to adjust the degradation rate of BPLPAT films.

TABLE 1

Conductivity of BPLP and BPLPAT films

| | Dry (S/cm) |
|---|---|
| BPLP | N/A |
| BPLPAT5% | 1.06 × 10$^{-7}$ |
| BPLPAT10% | 4.32 × 10$^{-7}$ |
| BPLPAT15% | 2.94 × 10$^{-6}$ |

Figure 4:
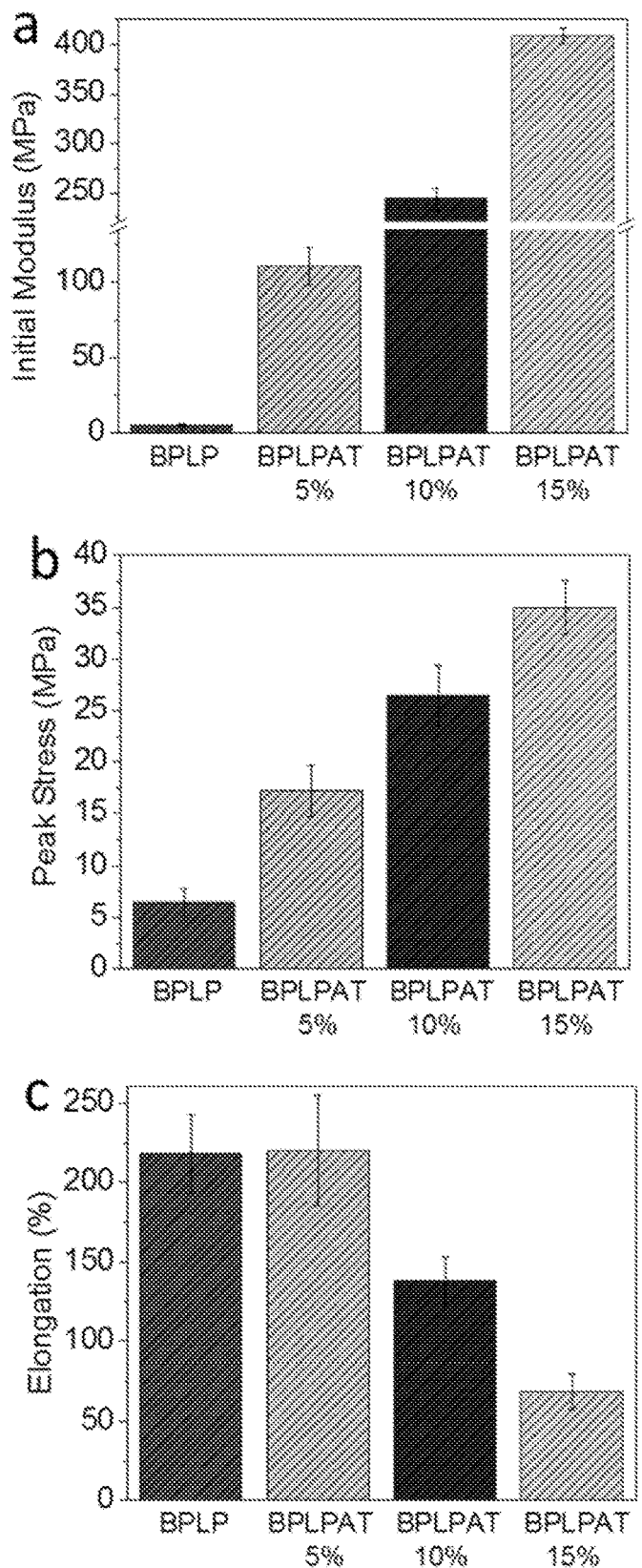
FIG. 4 shows mechanical properties of BPLPAT films and scaffolds. (a) Initial modules, (b) peak stress, and (c) elongation of BPLP and BPLPAT films under dry condition. (d) Initial modules, (e) peak stress, and (f) elongation of BPLP and BPLPAT films under wet condition. (g) Tensile-Strain curves of BPLP and BPLPAT films under dry condition. (g) Tensile-Strain curves of BPLP and BPLPAT films under wet condition. (i) Initial Modules and (j) peak stress of BPLP and BPLPAT scaffolds under wet condition.
Figure 4:
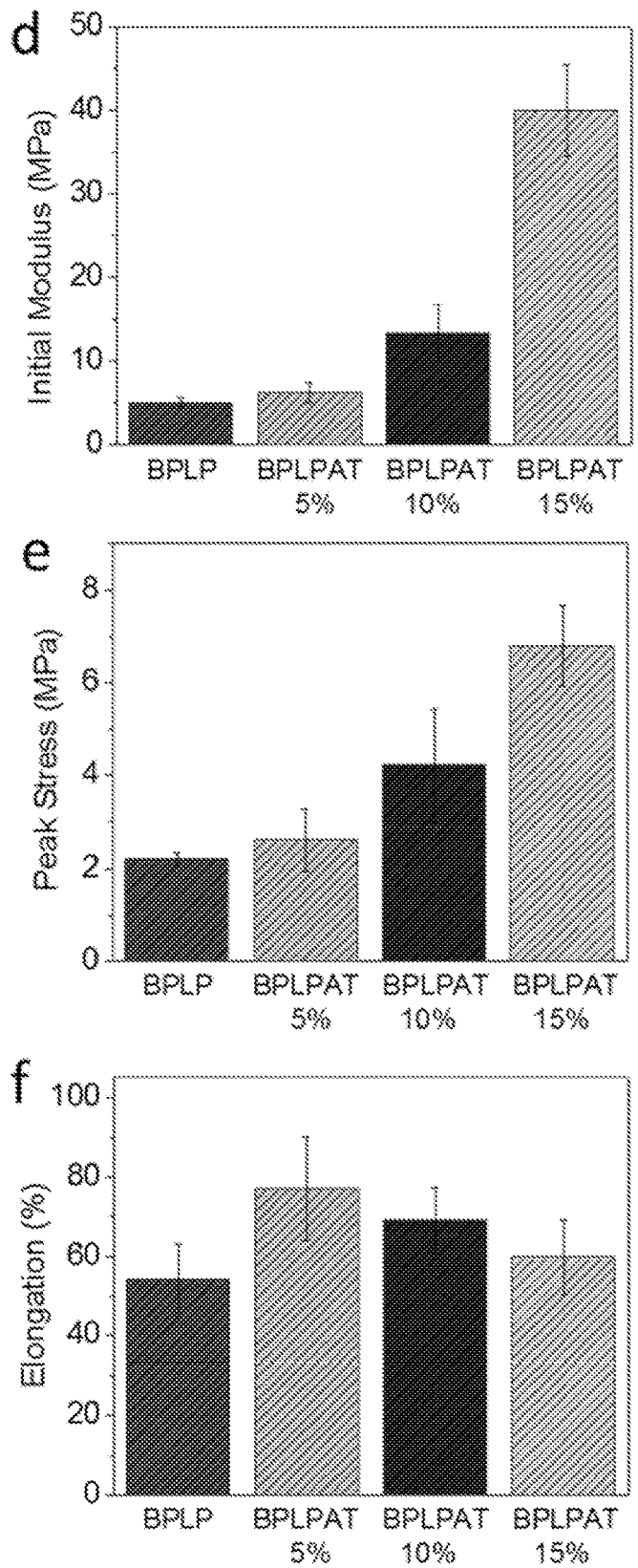
Figure 4:
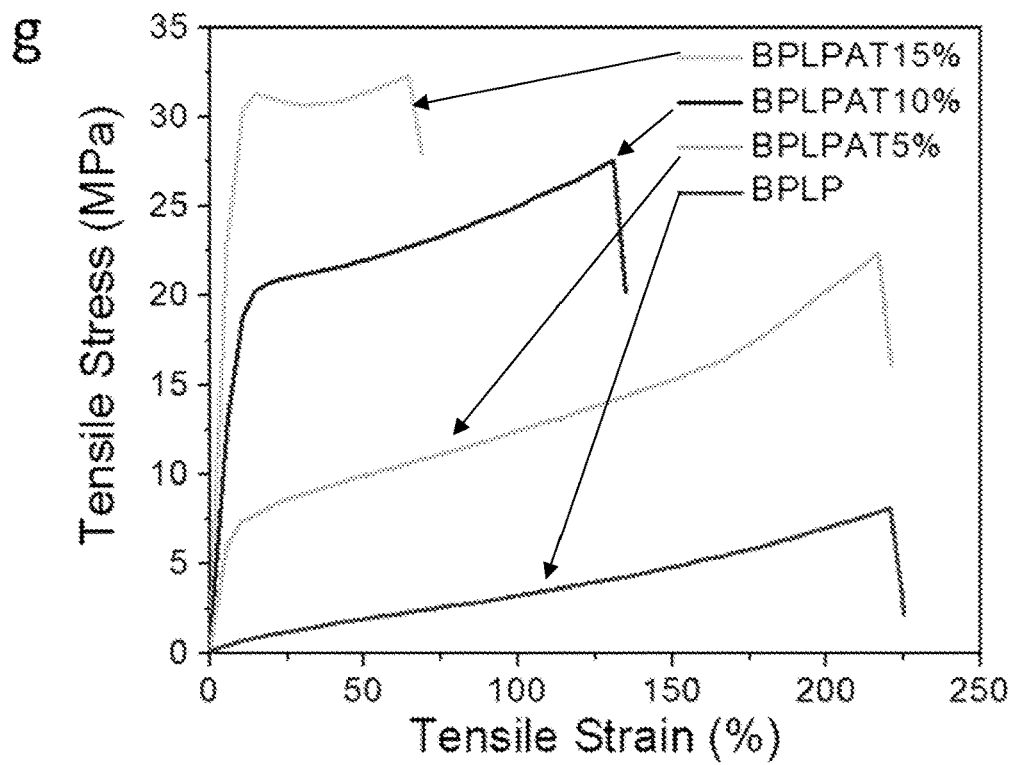
Figure 4:
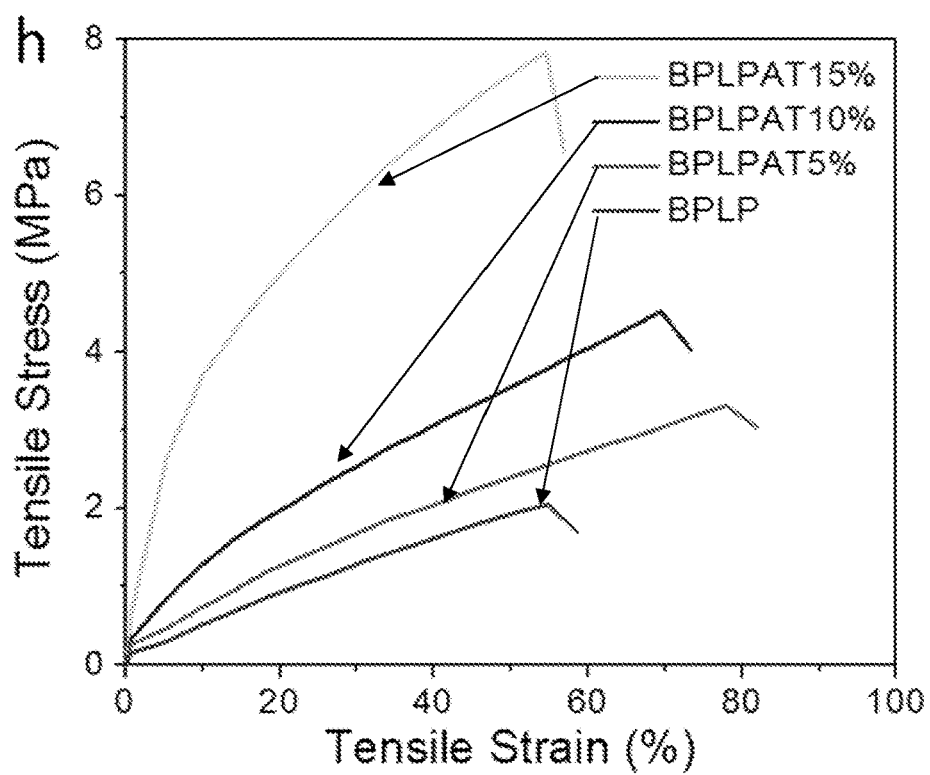
Figure 4:
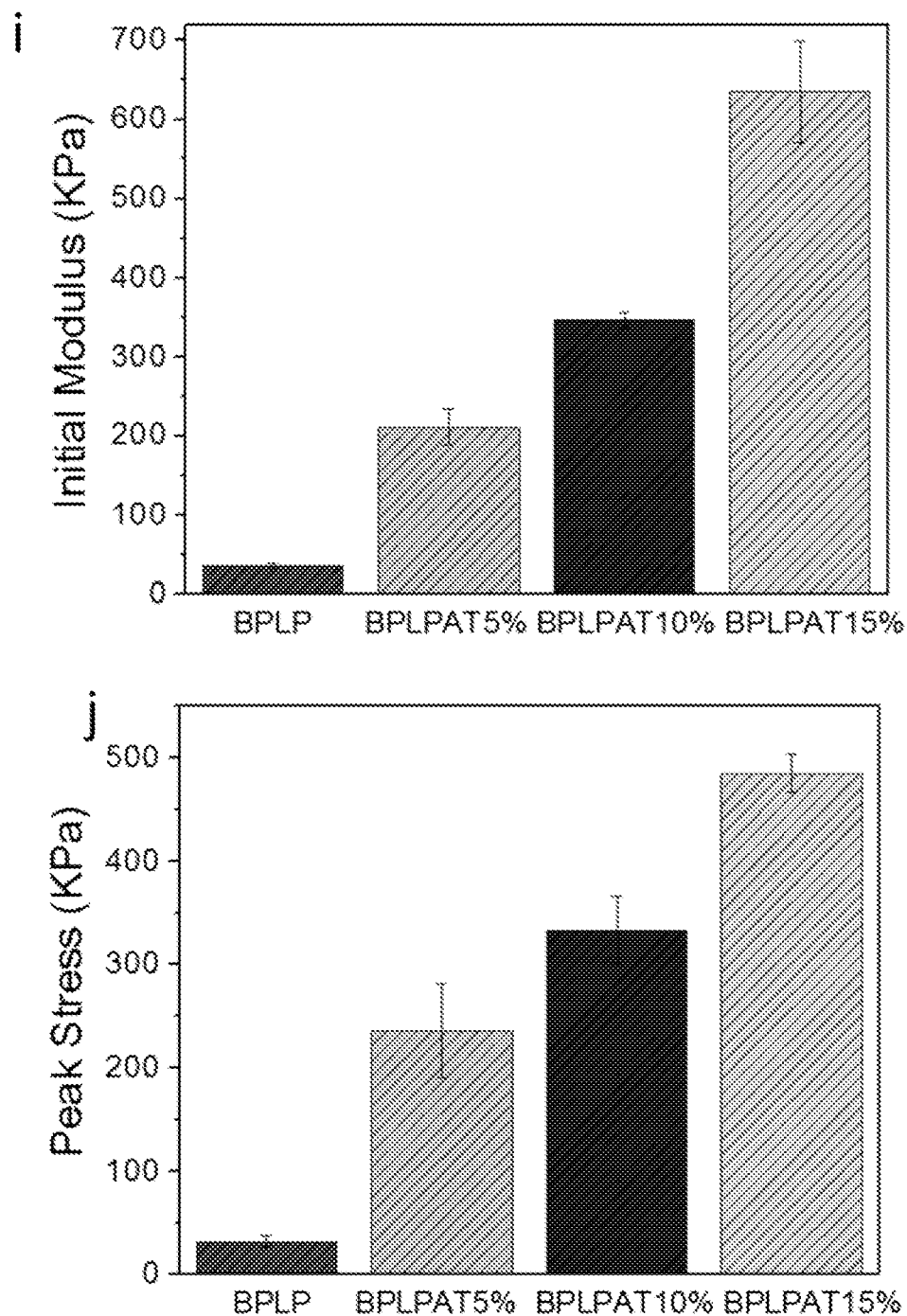

Mechanical Properties. Different tissues have specific mechanical properties, and cells react differently when material stiffness changes, thus biomaterials with appropriate mechanical properties are important for tissue engineering applications. The mechanical studies of BPLPAT materials are presented in FIG. 4. For dry BPLPAT polymer films, their initial modulus increased about 80 times from BPLP (5.21±1.15 MPa) to BPLPAT15% (409.24±7.75 MPa) (FIG. 4a). The increased AT content also led to the higher tensile stress (FIG. 4b) but lower tensile strain, except for BPLPAT5% that has comparable strain as BPLP (FIG. 4c). Mechanical properties of BPLPAT films were significantly regulated depending on the AT content, which are indicated by the shapes of tensile stress-strain curves (FIG. 4g). In detail, from BPLP to BPLPAT10% films, they present increased mechanical strengths but still keep the classical stress-strain curve for elastomers, while BPLPAT15% shows a curve for a flexible plastic. For biological applications, materials need to work in wet conditions. Thus, mechanical properties of wet films were also studied, and the tensile stress-strain curves are presented in FIG. 4h. After introducing AT, not only are the initial modulus and tensile stress increased (FIG. 4d-e); their elongation was also increased (FIG. 4f). While not intending to be constrained by any particular theory, this might be attributed to hydrogen bonds established between AT and BPLP structures. In addition, mechanical properties of BPLPAT scaffolds were also conducted through compression testing. The results indicate that the initial Modules and peak stress of BPLPAT scaffolds are also regulated by AT contents (FIGS. 4i and 4j). Therefore, a series of BPLPAT materials with highly tunable mechanical properties were easily achieved by changing AT content in polymers, which enabled BPLPAT polymers with wide potential in biomedical applications.

Figure 3:
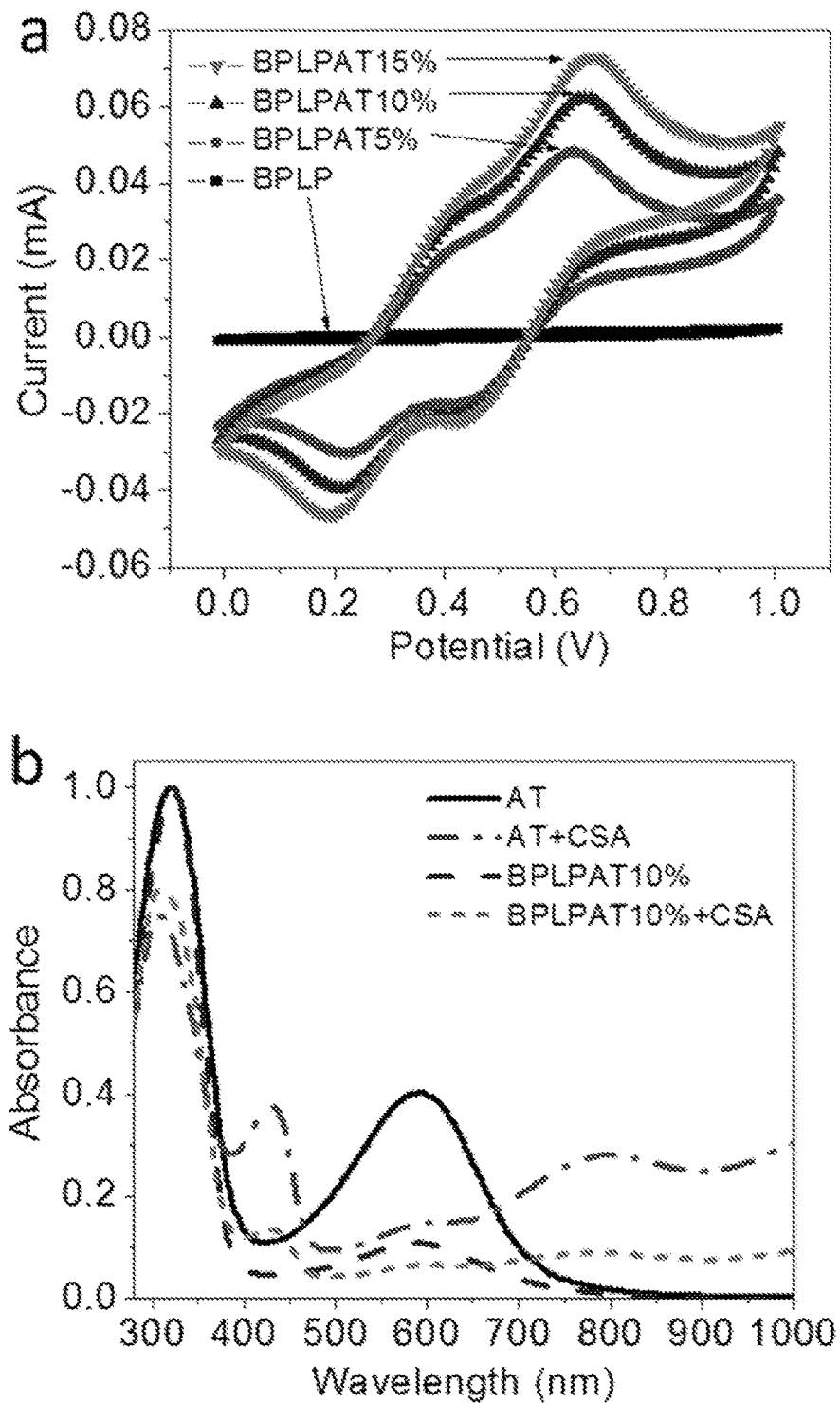
FIG. 3 shows electrochemical properties and in vitro degradation properties of BPLPATs. (a) The cyclic voltammogram (CV) curves of BPLPATs doped with CSA. (b) The UV spectra of AT, CSA doped AT, BPLPAT10%, and CSA doped BPLPAT10%. (c) In vitro degradation of BPLP and BPLPAT10% prepolymers. (d) In vitro degradation of BPLP and BPLPAT10% films.
Figure 3:
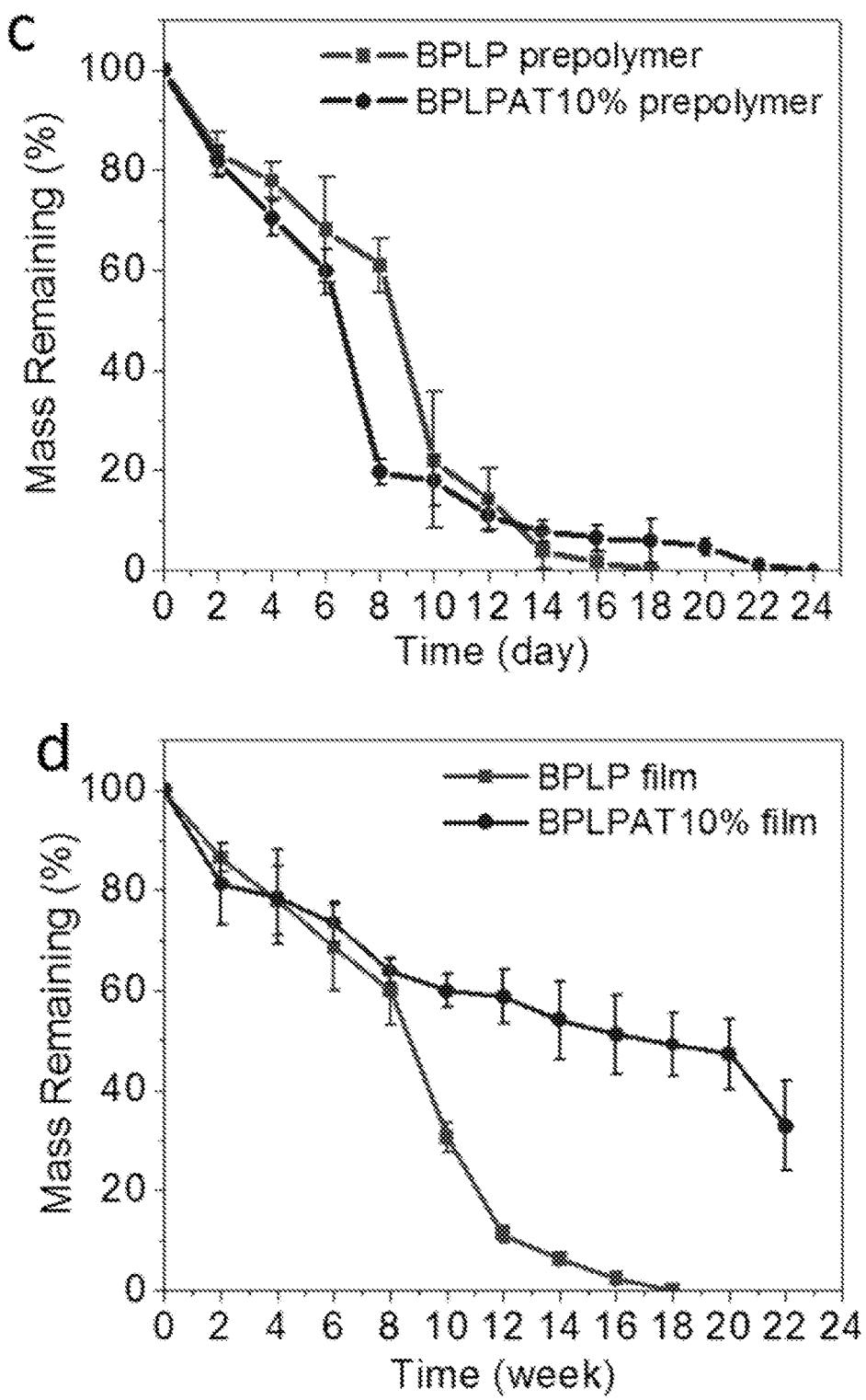
Figure 8:
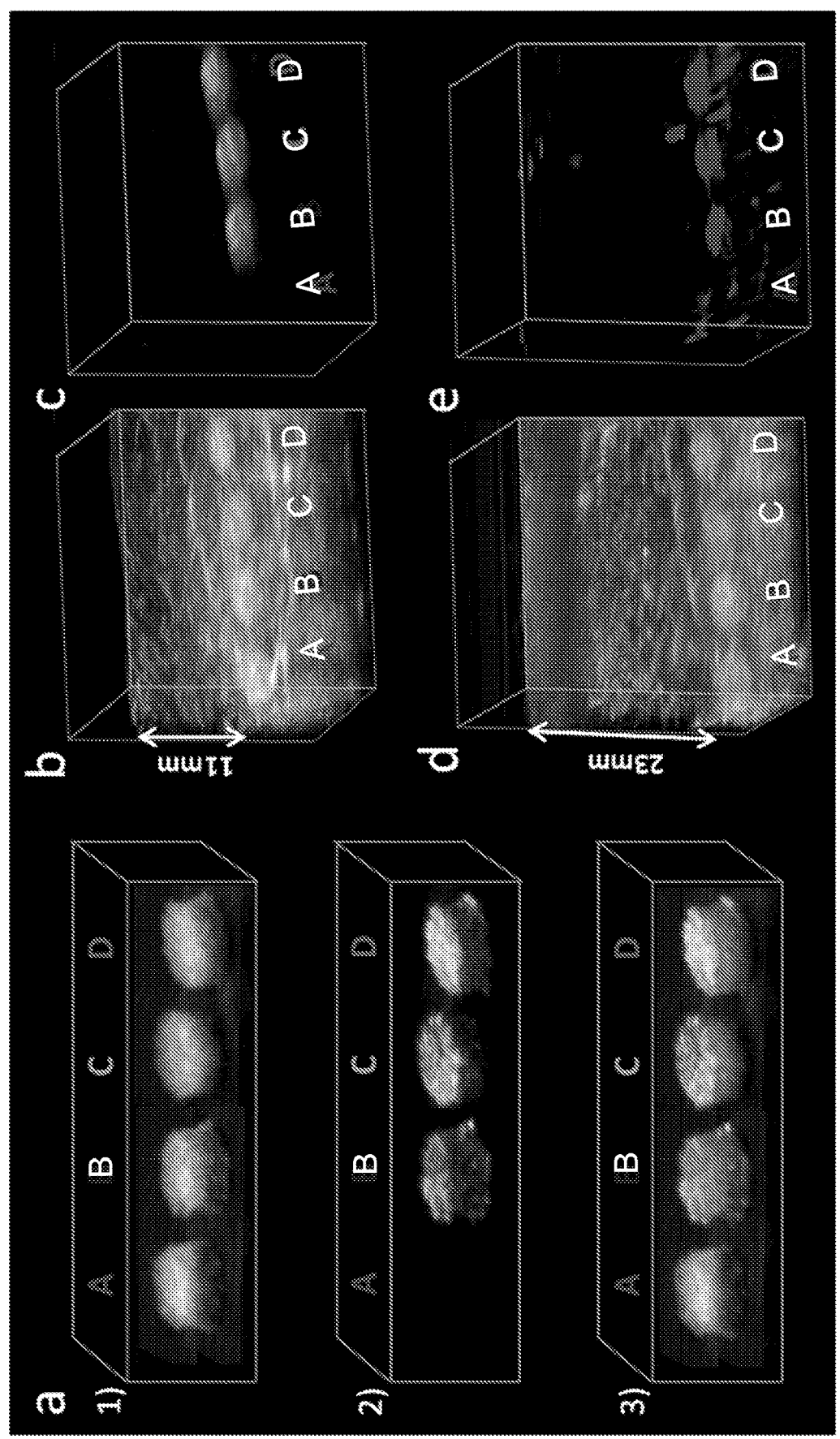
FIG. 8 shows ultrasound and PA imaging of BPLP and BPLPAT scaffolds. (a) PA images of BPLP and BPLPAT scaffolds embedded inside agar gel. (b) Ultrasound images and (c) PA images of BPLP and BPLPAT scaffolds under one layer of chicken breast tissue. (d) Ultrasound images and (e) PA images of BPLP and BPLPAT scaffolds under two layers of chicken breast tissue.

Imaging Properties of BPLPAT Scaffolds and Nanoparticles. BPLPAT cylinder scaffolds with the diameter of 7 mm, thickness of 3 mm, and interconnected pores were prepared by the traditional salt leaching method. Scaffolds of BPLP, BPLPAT5%, BPLPAT10%, and BPLPAT15% were imbedded inside agar gel to get quantative PA signals. PA intensities of BPLPAT scaffolds recorded at wavelengths from 680 to 920 nm are presented in FIG. 5a, which shows the scaffolds with higher AT content exhibit higher PA intensities. In FIG. 8a, 3D structures from ultrasound images (FIG. 8a1), PA images (FIG. 8a2), as well as their superimposed images (FIG. 8a3) are displayed. Ultrasound images helped to locate the sample positions; then, these images were overlaid with PA images. BPLP scaffold showed no noticeable PA signal, while all BPLPAT scaffolds exhibit PA images with high resolution. To explore the deep tissue imaging capacity of BPLPAT scaffolds, BPLP, BPLPAT5%, BPLPAT10%, and BPLPAT15% scaffolds were placed on a chicken breast tissue, and covered by one (~11 mm) or two pieces (~23 mm) of chicken breast tissues for PA imaging. In both experiments, ultrasound images of scaffolds become obscure because of the ultrasound signal from surrounding chicken tissue, which is a disadvantage for in vivo ultrasound imaging technique (FIGS. 8b and d). BPLPAT5%, BPLPAT10%, and BPLPAT15% scaffolds demonstrate excellent 3D PA images without any background noise under one layer of chicken tissue (FIG. 8e). The PA imaging performance of BPLPAT scaffolds declined under two layers of chicken tissues, which is shown in FIG. 8e with some background signals. In the superimposed images of ultrasound and PA (FIGS. 5f and g), PA imaging are applied to whole scaffolds of BPLPAT5%, BPLPAT10%, and BPLPAT15% under one layer of chicken tissue, while only the top part of scaffolds are imaged under two layers of chicken tissues due to the deep tissue penetration limitation of PA imaging.

Figure 5:
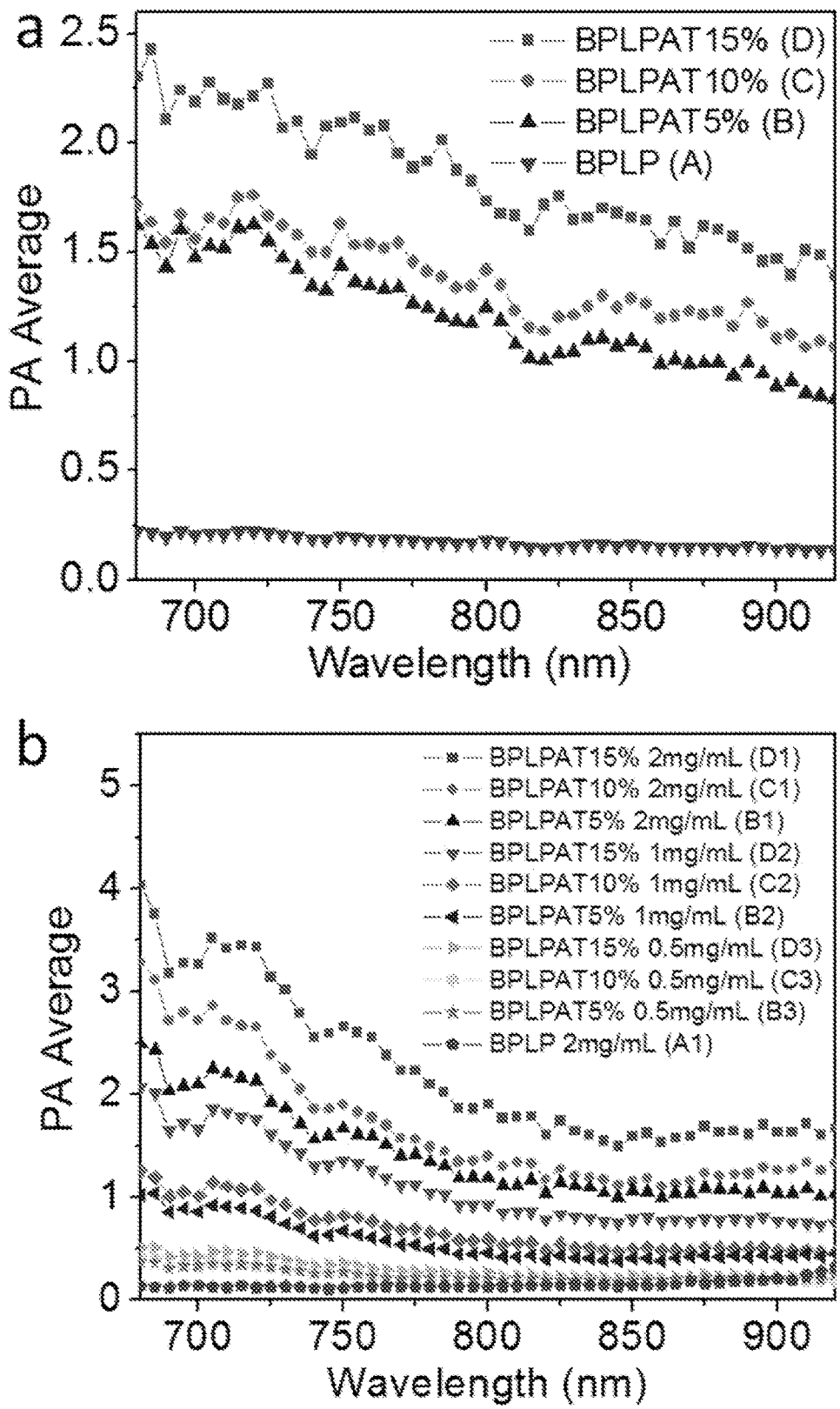
FIG. 5 shows PA and fluorescence imaging of BPLPAT scaffolds and nanoparticles. (a) PA intensity of BPLP and BPLPAT scaffolds (data shown from top to bottom corresponds directly with the legend from top to bottom). (b) PA intensity of BPLP and BPLPAT nanoparticles (data shown from top to bottom corresponds directly with the legend from top to bottom). (c), (d), and (e) experiment setup for deep tissue PA imaging of BPLP and BPLPAT scaffolds. (f) Overlaid ultrasound and PA images of BPLP and BPLPAT scaffolds under one layer of chicken breast tissue. (g) Overlaid ultrasound and PA images of BPLP and BPLPAT scaffolds under two layer of chicken breast tissue. (h) Overlaid ultrasound and PA images of BPLP and BPLPAT nanoparticles under a thin layer of chicken breast tissue. (i) Overlaid ultrasound and PA images of BPLP and BPLPAT nanoparticles under a thick layer of chicken breast tissue. (j) Fluorescent images of PC12 cells uptaken with BPLP and BPLPAT nanoparticles with blue fluorescence.
Figure 5:
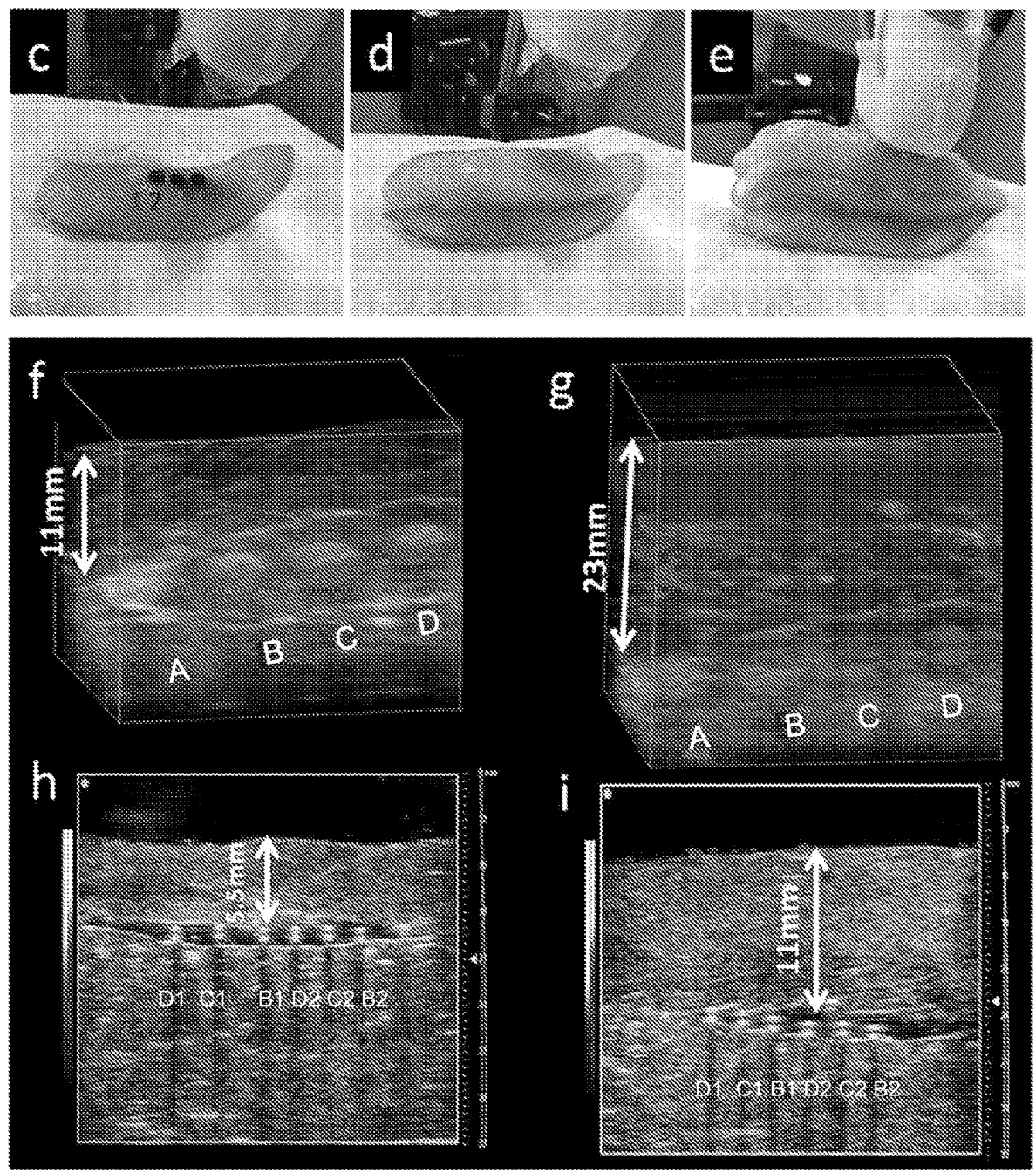
Figure 5:
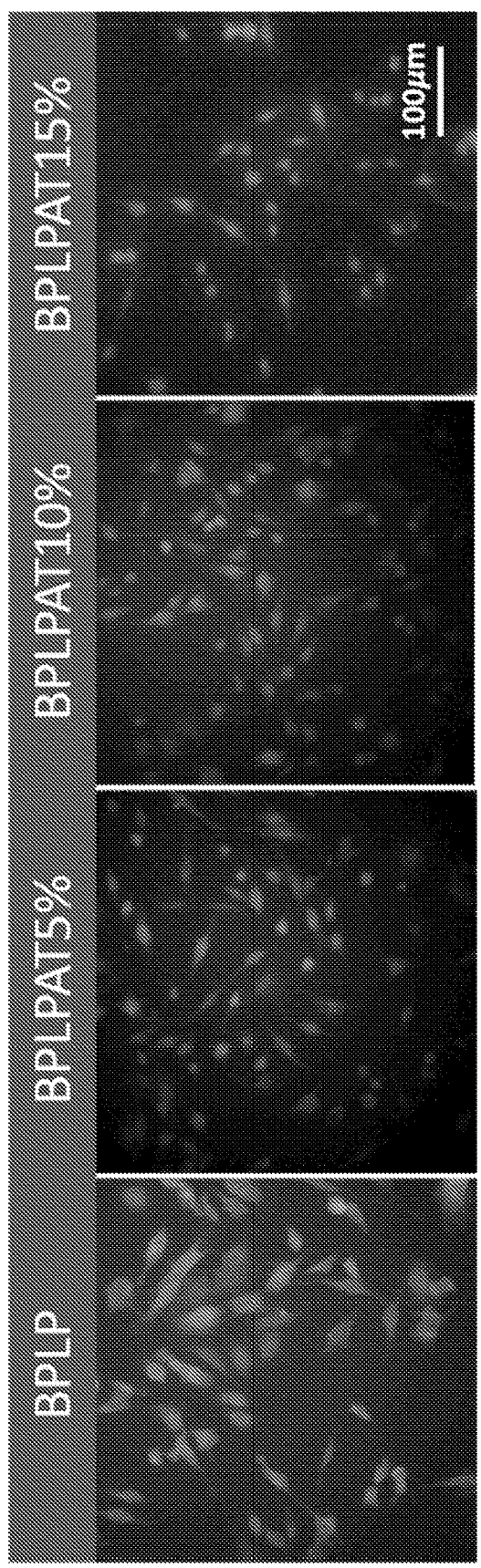
Figure 9:
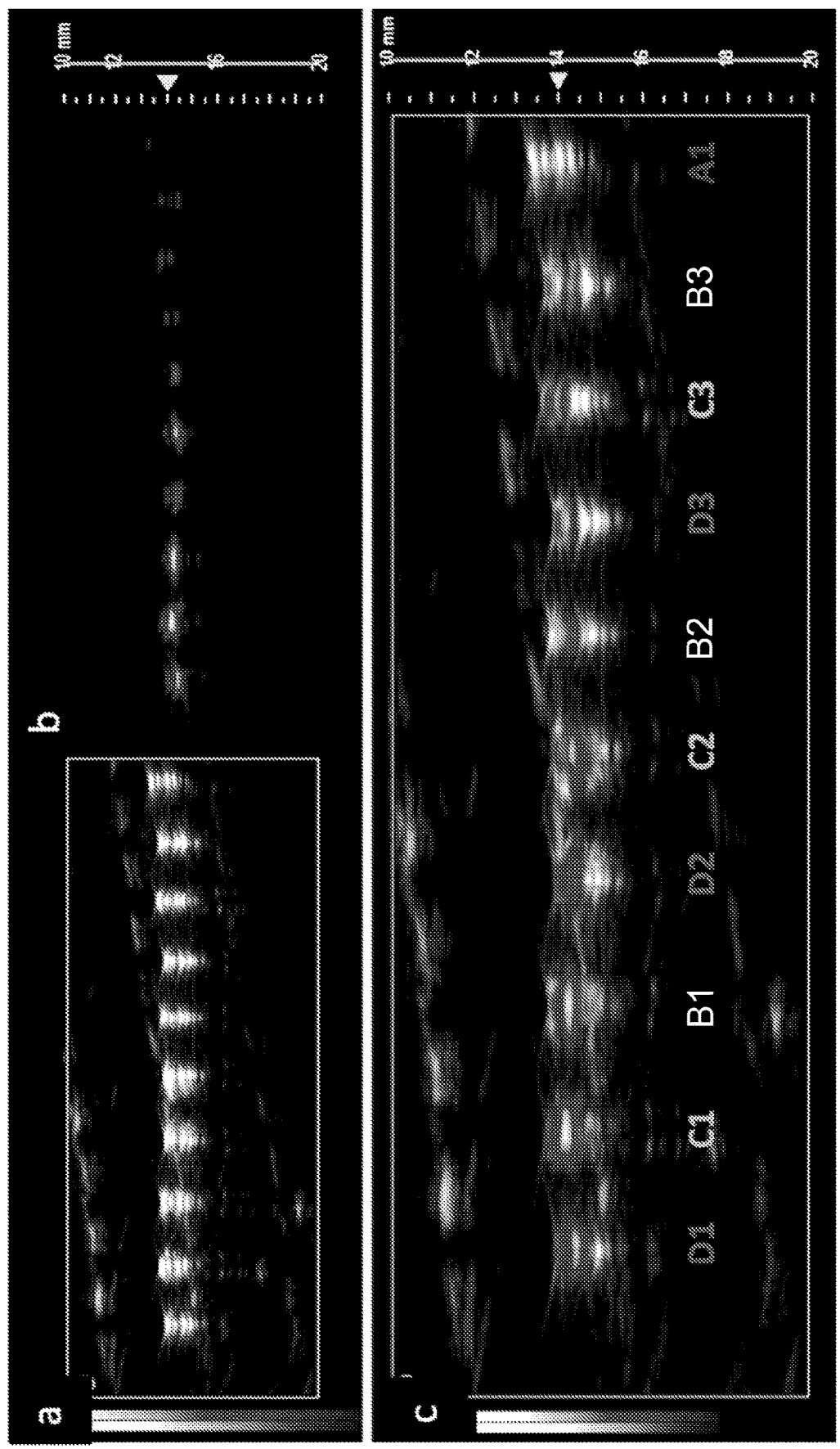
FIG. 9 shows PA imaging of BPLP and BPLPAT nanoparticles. (a) Ultrasound images of BPLP and BPLPAT nanoparticle solutions at various concentrations. (b) PA images of BPLP and BPLPAT nanoparticle solutions at various concentrations. (c) Overlaid ultrasound and PA images of BPLP and BPLPAT nanoparticle solutions at various concentrations.
Figure 10:
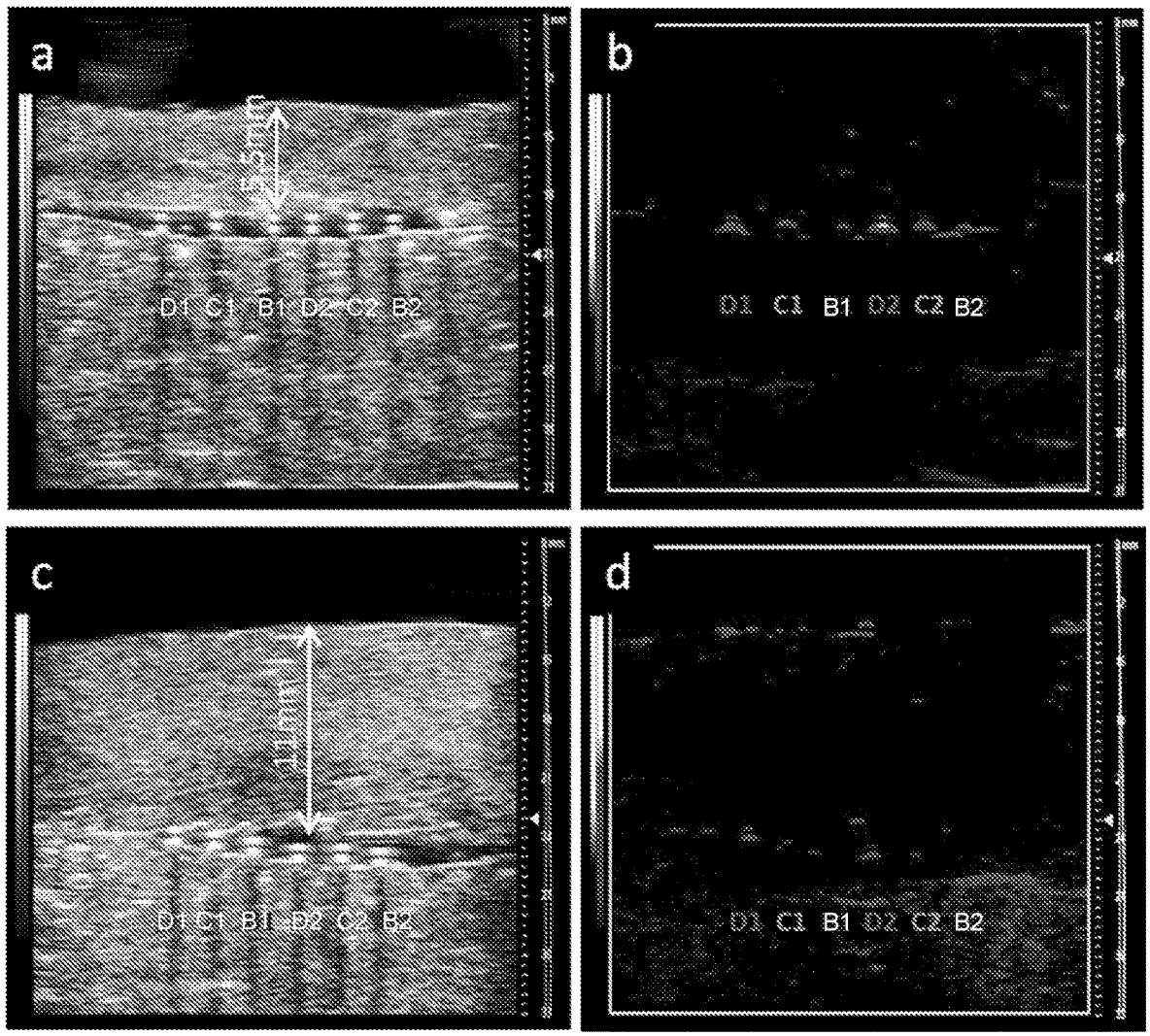
FIG. 10 shows PA imaging of BPLP and BPLPAT nanoparticles. (a) Ultrasound images of BPLP and BPLPAT nanoparticle solutions at various concentrations under a thin layer of chicken tissue. (b) PA images of BPLP and BPLPAT nanoparticle solutions at various concentrations under a thin layer of chicken tissue. (c) Ultrasound images of BPLP and BPLPAT nanoparticle solutions at various concentrations under a thick layer of chicken tissue. (d) PA images of BPLP and BPLPAT nanoparticle solutions at various concentrations under a thick layer of chicken tissue.

With the nano-precipitation method, BPLP, BPLPAT5%, BPLPAT10%, and BPLPAT15% nanoparticles with sizes of 164.3±6.9, 178.2±4.3, 182.6±2.0, and 181.9±5.7 nm are obtained, and all nanoparticles exhibit high stability based on their zeta potential values of −55.5±1.95, −60.2±0.6, −59.3±2.8, and −49.1±0.7 mV, respectively (Table 2). To study the PA imaging ability of BPLP and BPLPAT nanoparticles, nanoparticle solutions with different concentrations were first placed in NIR-inactive polyurethane (PU) tubes to get quantitative signal intensities at wavelength from 680 to 920 nm. As indicated in FIG. 5b, PA intensity of nanoparticle solutions decreases with lower AT content and lower concentration of each nanoparticle groups. The representative ultrasound images, PA images, and their overlaid images are presented in FIG. 9, which further confirmed the quantitative results. Deep tissue PA imaging of BPLP and BPLPAT nanoparticles were also conducted with chicken tissue (FIGS. 5h, 5i, and 10). BPLPAT5%, BPLPAT10%, and BPLPAT15% nanoparticle solutions at concentrations of 1 and 2 mg/mL demonstrate excellent PA imaging performance under a thin chicken lay of 5.5 mm, while the PA signal of BPLPAT5% nanoparticle at both concentrations decrease significantly when the chicken layer increased to 11 mm.

TABLE 2

Size and Zeta potential of BPLP and BPLPAT nanoparticles.

| Nanoparticles | BPLP | BPLPAT5% | BPLPAT10% | BPLPAT15% |
| --- | --- | --- | --- | --- |
| Size (nm) | 164.3 ± 6.9 | 178.2 ± 4.3 | 182.6 ± 2.0 | 181.9 ± 5.7 |
| Zeta potential (mV) | −55.5 ± 1.95 | −60.2 ± 0.6 | −59.3 ± 2.8 | −49.1 ± 0.7 |

Figure 11:
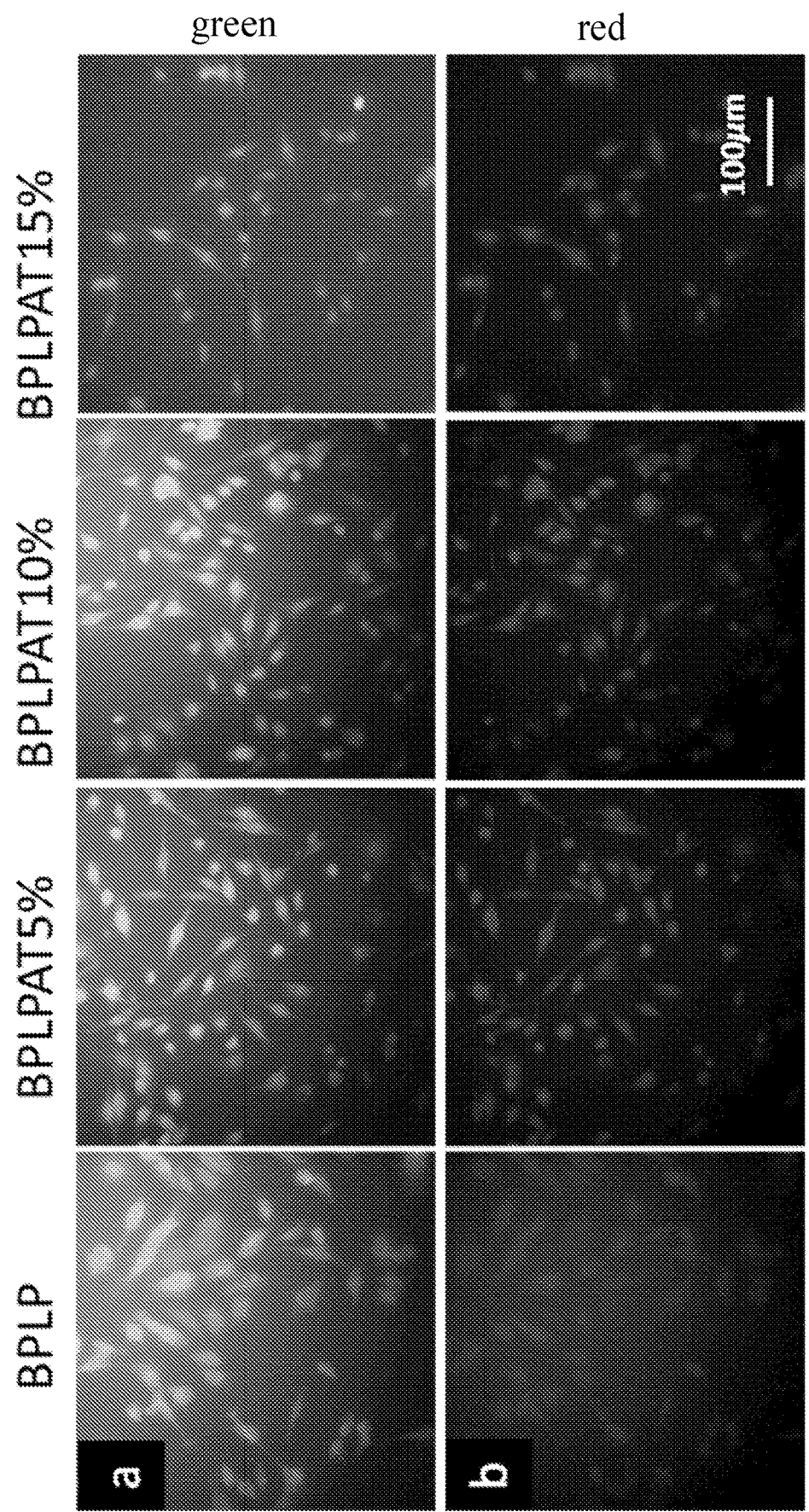
FIG. 11 shows fluorescent images of PC12 cells uptaken with BPLP and BPLPAT nanoparticles with (a) with green fluorescence, and (b) red fluorescence.
Figure 12:
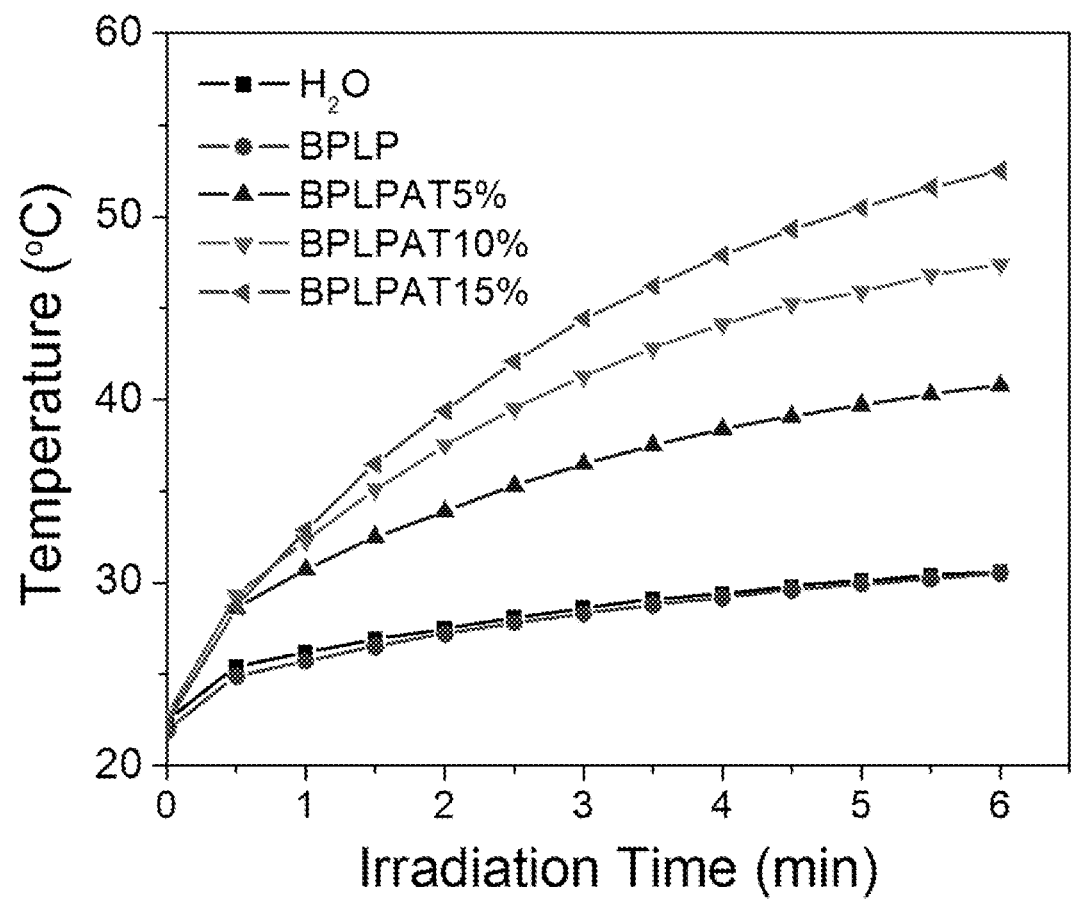
FIG. 12 shows temperature rise traces of the BPLP and BPLPAT nanoparticles under NIR illumination, deionized (DI) water works as the control.

Cellular uptake of BPLP and BPLPAT nanoparticles was also conducted to investigate their fluorescence cellular imaging capacity. The fluorescent images of BPLP and BPLPAT nanoparticles up-taken by PC12 cells were recorded and imaged with a fluorescence microscope to confirm their cell labeling properties (FIGS. 5j and 11). Although BPLPATs have lower fluorescent intensity than BPLP, nanoparticle stained cells still presented strong fluorescence images under the fluorescent microscope with DAPI filter, GFP filter, and Cy3 filter. In order to investigate the photothermal properties of BPLPAT nanoparticles, BPLPAT nanoparticle solutions and BPLP nanoparticle solution with the same concentration of 0.5 mg/mL were exposed to an 808-nm NIR laser at a power density of 1.5 W/cm$^2$, DI water was set as a control. FIG. 12 shows the time-dependent UV-vis spectra of as a function of NIR irradiation time. Apparent AT content dependent temperature increases of BPLPAT nanoparticles were found under laser irradiation, while BPLP nanoparticle solution and pure water showed little change. The high NIR absorbance coefficient and great photothermal performance of BPLPAT nanoparticles demonstrate their potential for use as a nanomaterial for thermal treatment of cancers.

Figure 6:
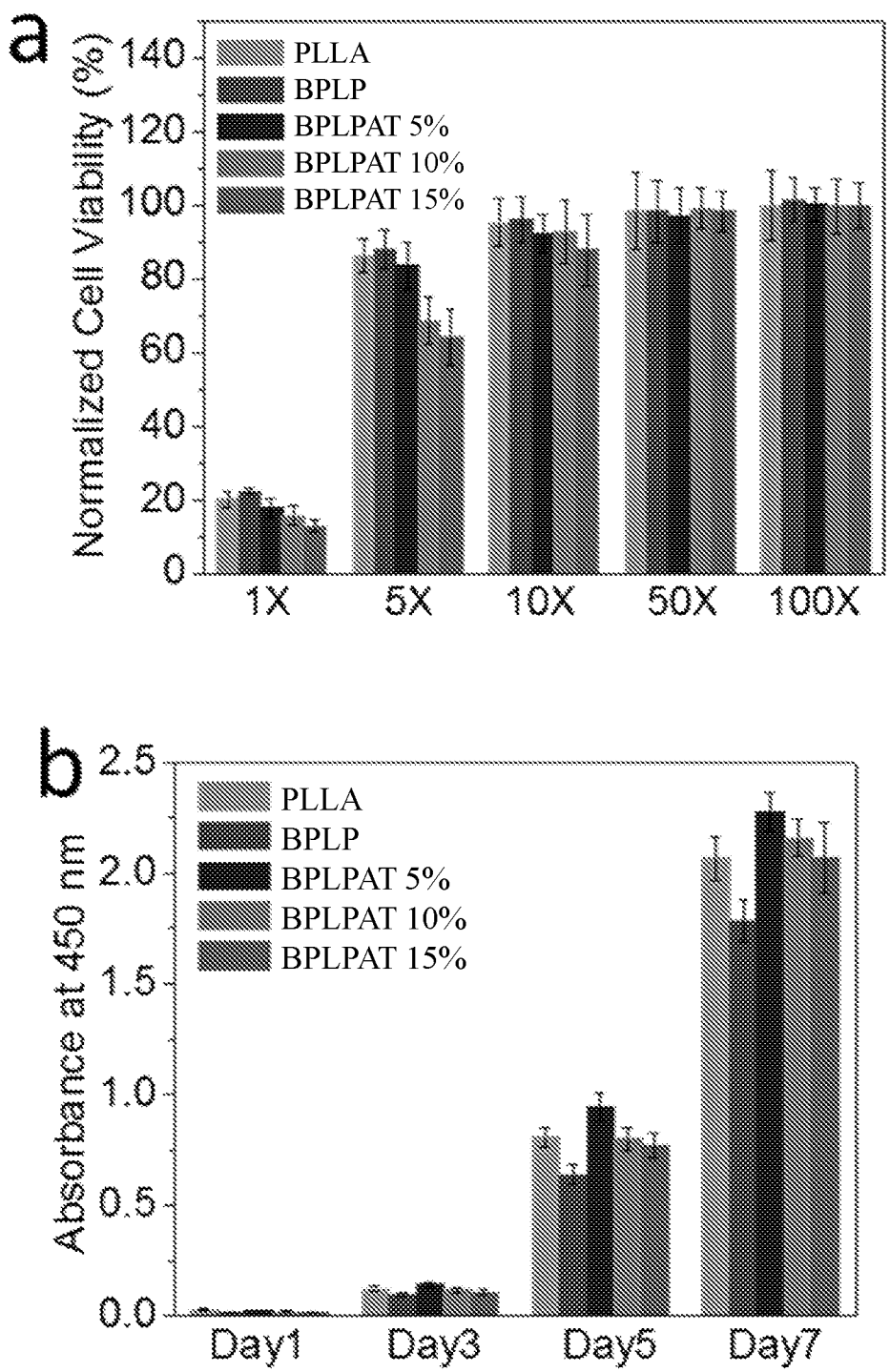
FIG. 6 shows in vitro cell culturing and in vivo foreign body response studies on BPLPAT materials. (a) Cytotoxicity degradation products of BPLP and BPLPATs, PLLA film as a control (each set of five columns represents from left to right, in the following order, PLLA, BPLP, BPLPAT5%, BPLPAT10%, and BPLPAT15%). (b) PC12 cell proliferation studies on BPLP and BPLPAT films for 7 days, PLLA film as a control (each set of five columns represents from left to right, in the following order, PLLA, BPLP, BPLPAT5%, BPLPAT10%, and BPLPAT15%). (c) Averaged total (each set of four columns represents, from left to right in the following order, PLLA, BPLP, BPLPAT5%, and BPLPAT10%) and (d) CD 11b positive cell numbers in a 200×200 μm² square region near the implant films (each set of four columns represents, from left to right in the following order, PLLA, BPLP, BPLPAT5%, and BPLPAT10%). (e) Electrical stimulation study of PC12 cells on BPLP and BPLPAT films. (f) Electrical stimulation study of PC12 cells on BPLP and BPLPAT scaffolds.
Figure 6:
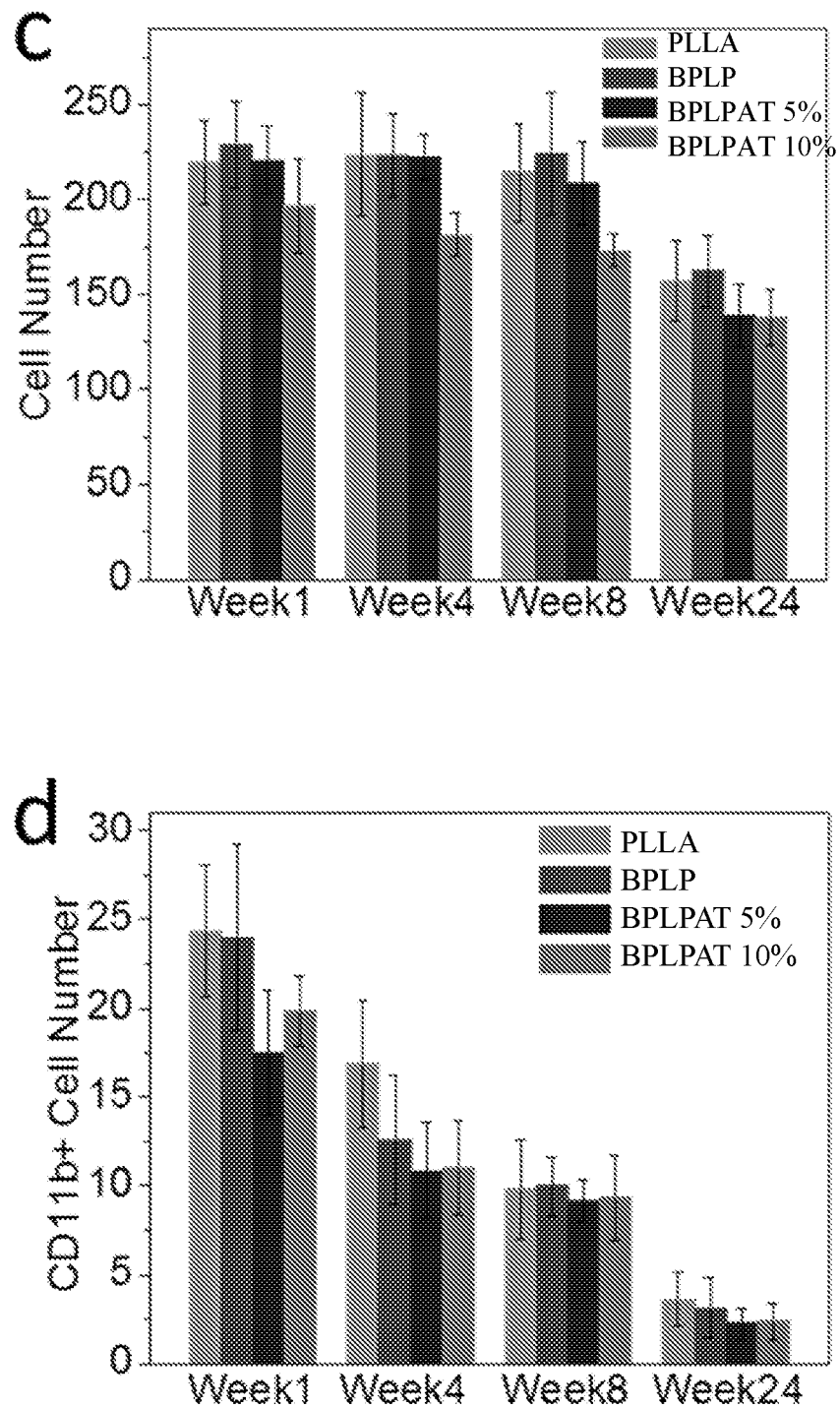
Figure 6:
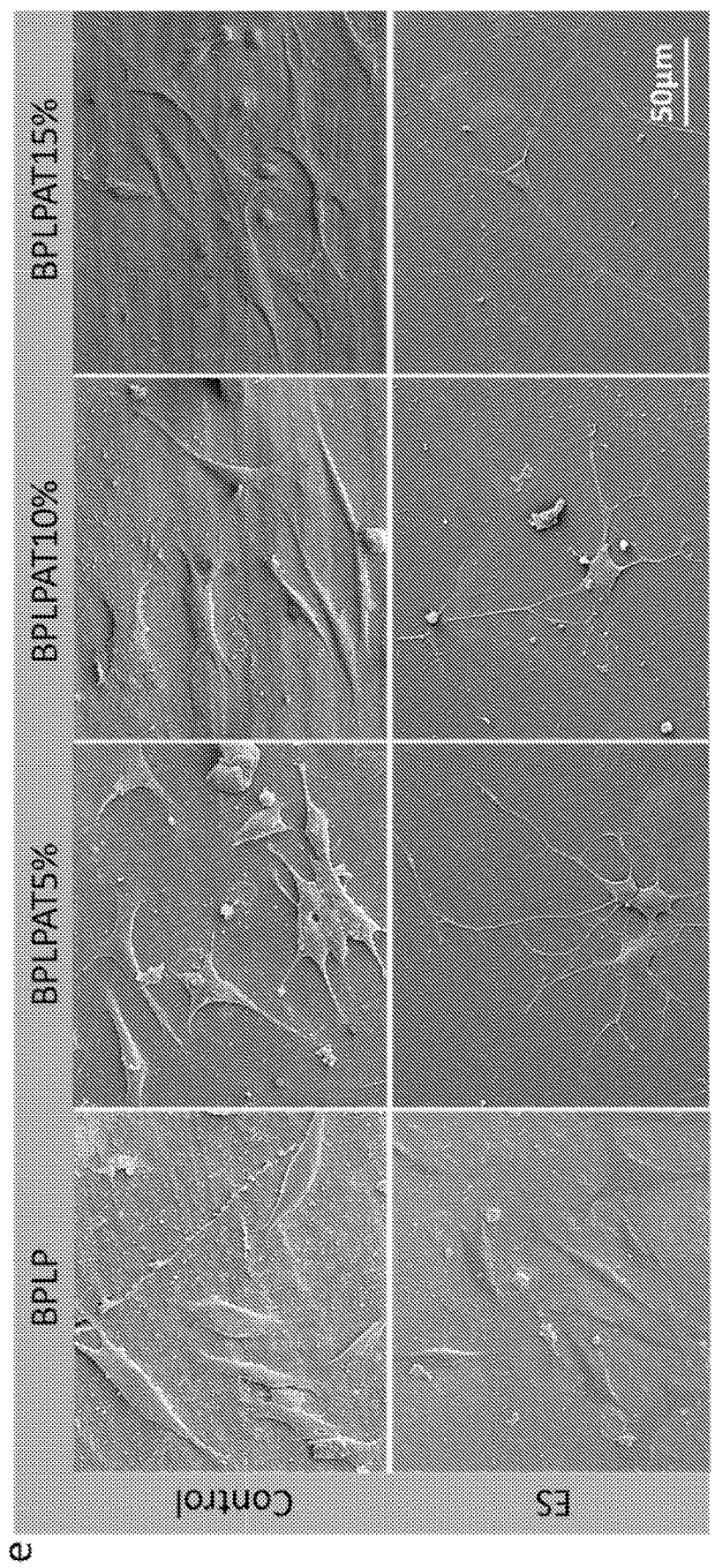
Figure 6:
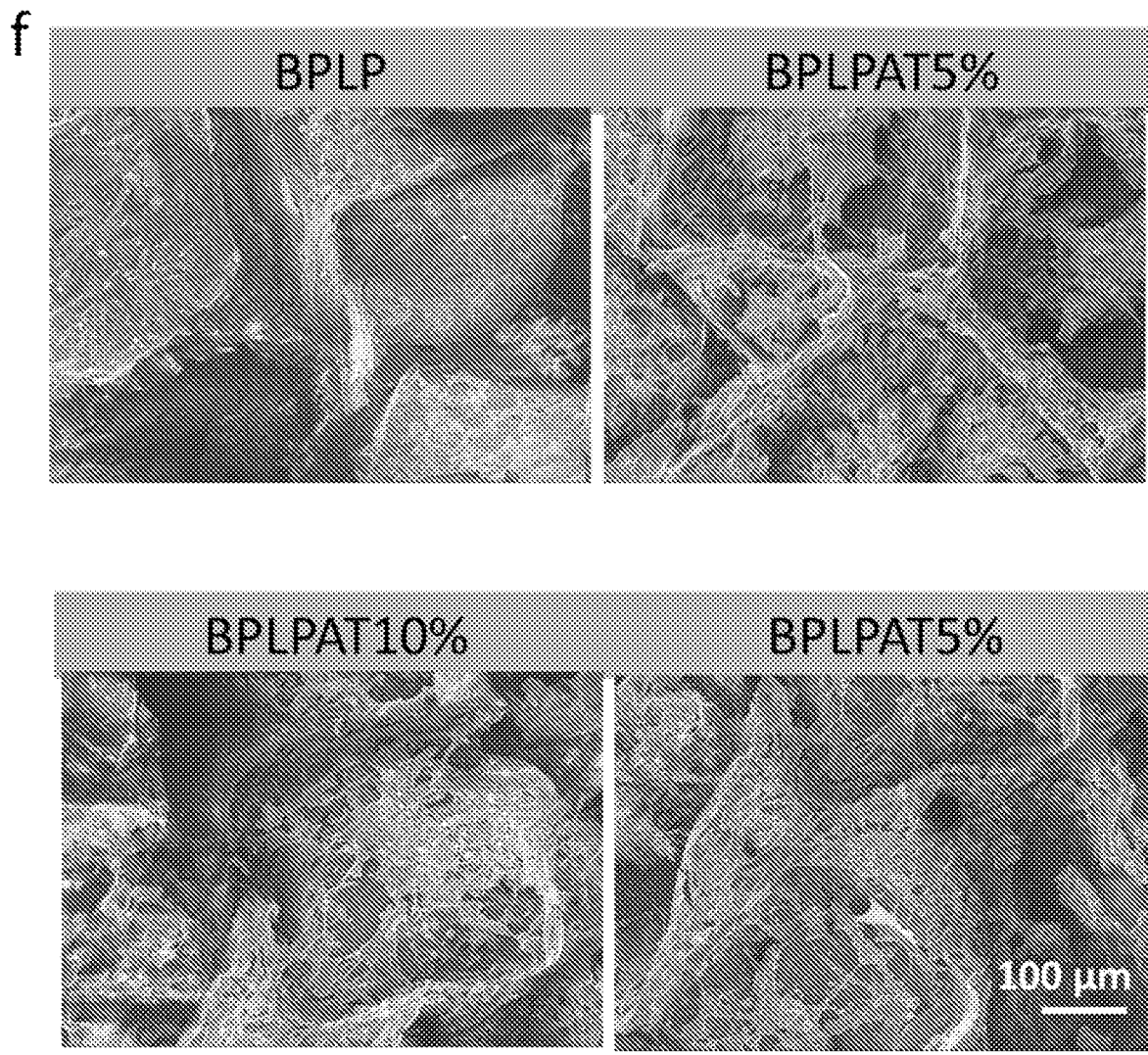

In vitro cytotoxicity, In vivo foreign body response, and electrical stimulation study of cells on BPLPAT films and scaffolds. For in vitro cell culture, rat pheochromocytoma cell line (PC12) was studied. In cytotoxicity study, PLLA was used as control. The results indicated that after 10 times dilution of the original concentration (0.1 g/mL in 1M NaOH), all degradation products are nontoxic (FIG. 6a). In cell proliferation study (FIG. 6b), PC12 cells were cultured on a series of BPLPAT films (BPLP, BPLPAT5%, BPLPAT10%, and BPLPAT15) for 7 days. BPLPAT films significantly promoted the proliferation of PC12 cells when compared with BPLP. However, with the increase of AT content, BPLPAT10% and BPLPAT15% films showed decreased cell proliferation effects compared to BPLPAT5%, which caused by the toxicity of released AT. Thus, an appropriate ratio of AT in BPLPAT films could optimize the proliferation of PC12 cells. In vitro cell culture studies confirmed the cytocompatibility of BPLPAT degradation products and BPLPAT films, as well as their capacity for the promotion of PC12 proliferation.

Figure 13:
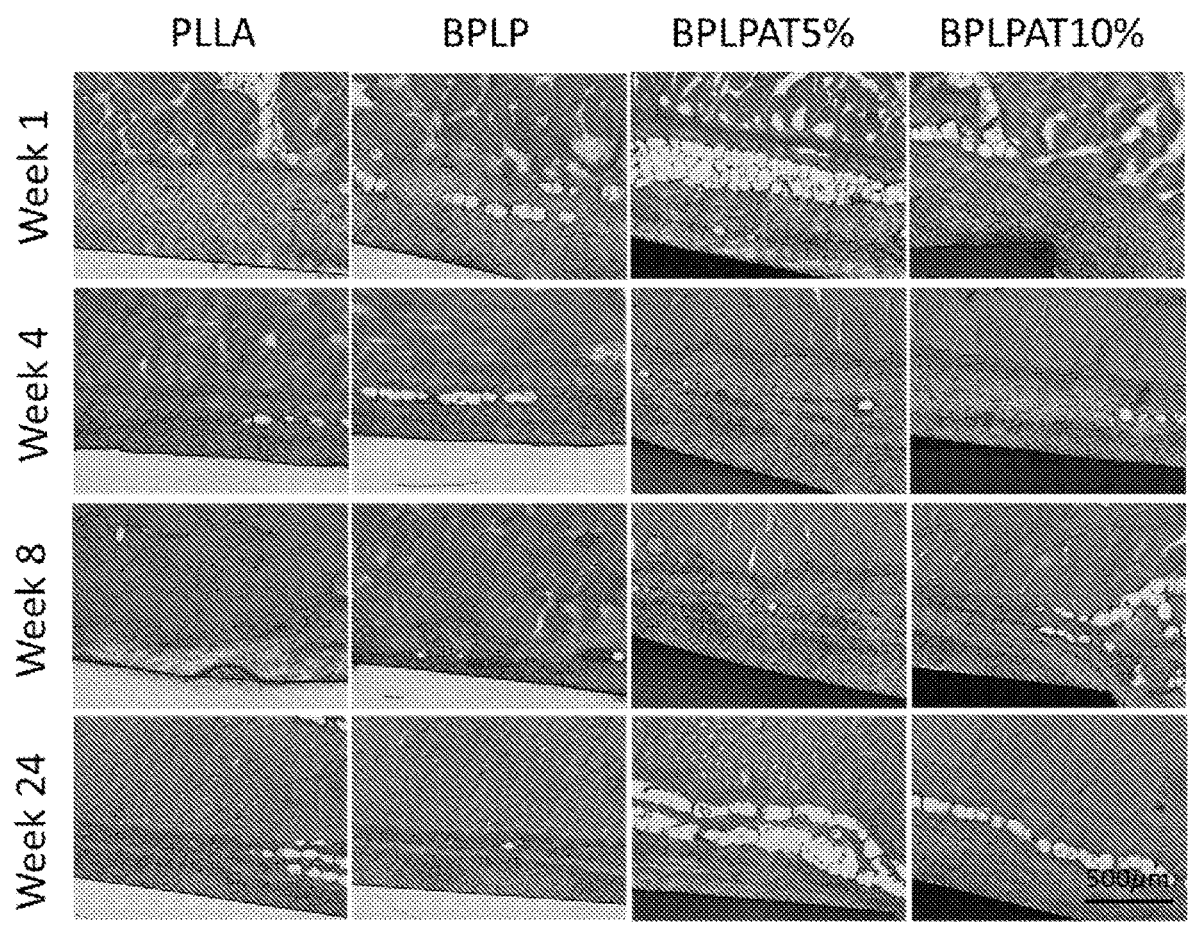
FIG. 13 shows foreign body response evaluations. Images of H&E (hematoxylin and eosin) staining of sections of subcutaneously implanted polymer films (PLLA, BPLP, BPLPAT5%, and BPLPAT10%) with surrounding tissues. Samples were harvested at 1 week, 4 weeks, 8 weeks, and 24 weeks following implantation.
Figure 14:
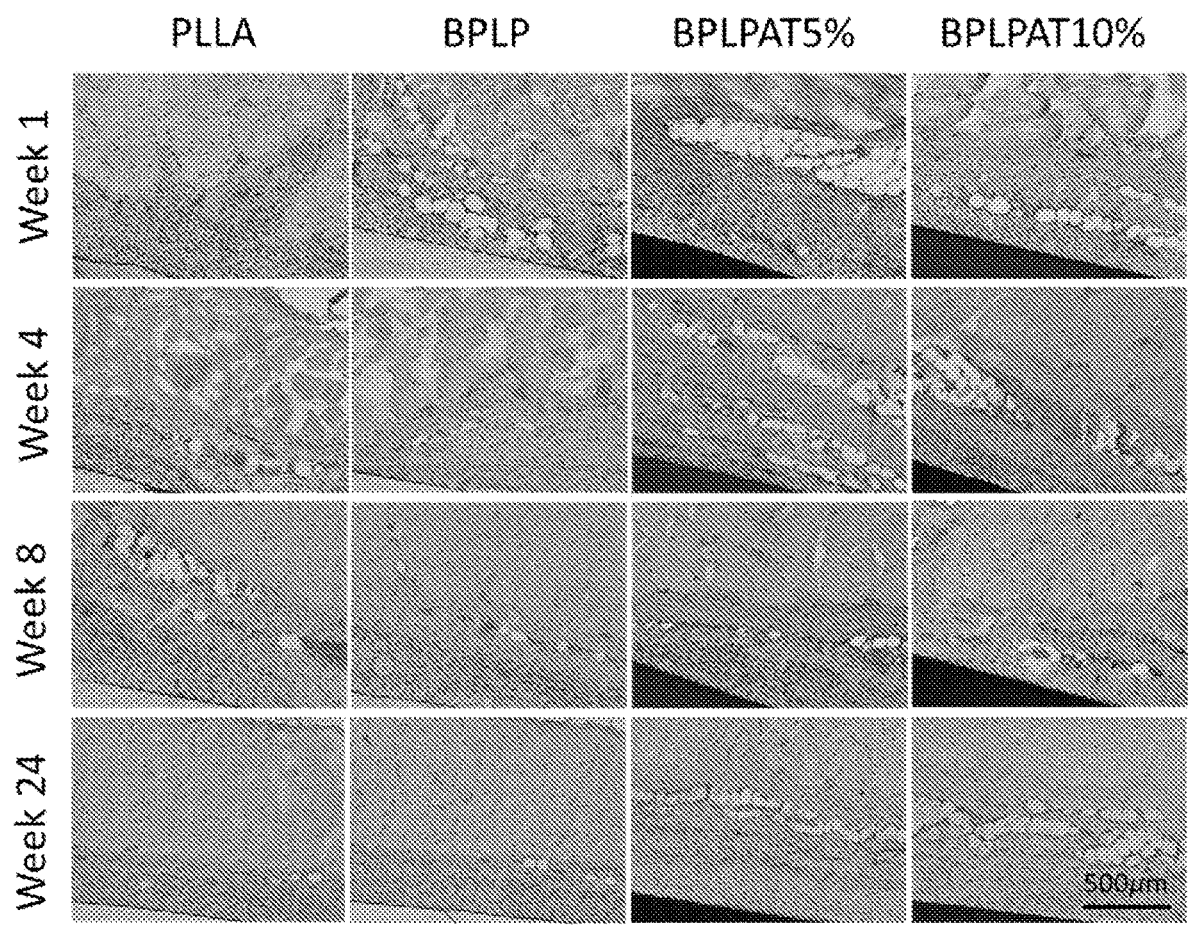
FIG. 14 shows foreign body response evaluations. Representative images of immunohistochemical (for CD11b) staining of sections of subcutaneously implanted polymer films (PLLA, BPLP, BPLPAT5%, and BPLPAT10%) with surrounding tissues. Samples were harvested at 1 week, 4 weeks, 8 weeks, and 24 weeks following implantation.

The in vivo foreign body response of BPLPAT films was studied by a subcutaneous implantation of BPLPAT5% and BPLPAT10% in SD rats using BPLP and PLLA as controls. As shown in FIGS. 13 and 14, all samples implanted for 1 week produced a slight acute inflammatory response, which is a general process that is expected and consistent with the introduction of a foreign material into the body and can be confirmed by the cell infiltration (H & E staining, FIG. 13) as well as the appearance of CD11b positive cells (CD11b staining, FIG. 14) in the tissues surrounding the polymer films. All samples implanted after 8 weeks produced a fibrous capsule between the films and muscle indicating minimal inflammatory reactions. Quantitative cell counting study indicates that total cell densities and CD11b positive cell densities surrounding different polymer film implants declined over time (FIGS. 6c and 6d). One interesting thing is, BPLPAT5% and BPLP10% films exhibit less total cell densities and CD11b positive cell densities at each time points. After 24 weeks of implantation, most of the cells surrounding the all implanted samples were fibroblast cells. CD11b positive cells were rarely seen after 24 weeks, indicating that minor chronic inflammatory reaction took place. The mild inflammatory response indicate that BPL-PAT films and their degradation products present better biocompatibility than the controls, BPLP and PLLA.

To test the electrical stimulation effect on PC12 cells differentiation, BPLP, BPLPAT5%, BPLPAT10%, and BPL-PAT15% films were all studied, and films without electrical stimulation were used as controls. Scanning electron microscope (SEM) (FIG. 6e) were applied to observe cell morphologies. The results indicated that BPLPAT films without electrical stimulation could promote neurites formation when compared with BPLPs, while electrical stimulation helped to generate more and longer neurites. Afterwards, BPLP, BPLPAT5%, BPLPAT10%, and BPLPAT15% scaffolds were also used to study the PC12 cell growth and differentiation properties under electrical stimulation. In FIG. 6f, SEM images present that PC12 cells are able to cover the surface very well and penetrate deep into the porous scaffold. Also, the branched and extended neurites indicate that cells grow on BPLPAT scaffolds show better differentiation effects.

It will be recognized from the foregoing that advanced biomaterials possessing both therapeutic and imaging functionalities are strongly desired for improving the safety, effectiveness, and specificity of disease treatments. The present disclosure demonstrates a biodegradable citrate-based biomaterial platform, with intrinsic electrical conductivity and dual-modal photoacoustic/fluorescent imaging capability, tunable mechanical properties, and programmable degradation profiles. BPLPAT polymers, due to their rich fabrication flexibilities, were prepared as films, scaffolds and nanoparticles. The polymers' favorable electroactivity successfully enabled BPLPAT films and scaffolds to promote proliferation and differentiation of PC12 cells. Dual imaging properties ensured that BPLPAT nanoparticles and scaffold would be detected under thick tissues, and that 3D images for BPLPAT scaffolds would be generated. By employing BPLPAT polymers, multiple implants or devices meeting requiring mechanical and functional properties can be designed for biomedical applications.

Although the present disclosure has been described with respect to one or more particular embodiments and/or examples, it will be understood that other embodiments and/or examples of the present disclosure may be made without departing from the scope of the present disclosure.

The invention claimed is:

1. A compound having a structure:

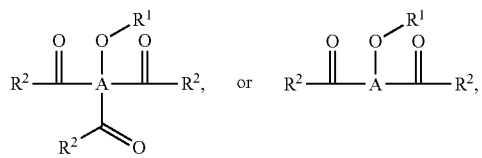

wherein
A is an aliphatic group,
$R^1$ is in each case independently selected from:
 i) H;
 ii) a biocompatible multifunctional carboxylic acid moiety covalently bonded to a conductive oligomer group/moiety;
 iii) a biocompatible multifunctional carboxylic acid group covalently bonded to a polyol; and
 iv) a biocompatible multifunctional carboxylic acid group;
 v) a linker moiety/group,
 vi) a linker moiety covalently bonded to a conductive oligomer group/moiety, and/or a polyol group/moiety;
$R^2$ is independently selected from:
 i) —OH,
 ii) a polyol group,
 iii) a conductive oligomer group,
 iv) a polyol moiety covalently bonded to a biocompatible multifunctional carboxylic acid group,
 v) a polyol covalently bonded to a biocompatible multifunctional carboxylic acid group, said biocompatible multifunctional carboxylic acid group being covalently bonded to one or more of a conductive oligomer group, a linker group, a biocompatible multifunctional carboxylic acid group, or polyol group;
 vi) a polyol covalently bonded to a linker group said linker group being covalently bonded to one or more of a conductive oligomer group, a linker group, biocompatible multifunctional carboxylic acid group, or polyol group;
wherein the compound comprises an oligomer covalently bonded to one or more conductive oligomeric groups, wherein the conductive oligomeric group is aniline tetramer.

2. The compound of claim 1, wherein the biocompatible multifunctional carboxylic acid moiety comprises a citric moiety and wherein the polyol is a diol.

3. The compound of claim 2, wherein the diol is selected from the group consisting of ethylene glycol, 1,3-propanediol, 1,4-butanediol, 1,5-pentanediol, 1,3-pentanediol, 1,6-hexanediol, 1,2-hexanediol, 1,5-hexanediol, 2-butene-1,4-diol, and 2-butyn-1,4-diol, 1,8-octanediol, 1,10-decanediol, 1,12-dodecanediol, polyethylene glycol, and polypropylene glycol.

4. The compound of claim 1, wherein the linker is selected from the group consisting of amino acids, aminothiols, aryl amines, and combinations thereof.

5. The compound of claim 1, wherein the one or more conductive oligomeric groups are present at 0.1 to 50 mol % relative to the biocompatible multifunctional carboxylic acid group.

6. The compound of claim 1, having a molecular weight of 500 to 10,000 g/mol.

7. A photoluminescent compound prepared by a process comprising the steps:
 1) forming a reaction mixture; and
 2) heating the reaction mixture to produce the photoluminescent compound;
  wherein the reaction mixture comprises a monomer mixture consisting of
  (a) citric acid;
  (b) a polyol, wherein the polyol is selected from the group consisting of ethylene glycol, 1,3-propanediol, 1,4-butanediol, 1,5-pentanediol, 1,3-pentanediol, 1,6-hexanediol, 1,2-hexanediol, 1,5-hexanediol, 2-butene-1,4-diol, and 2-butyn-1,4-diol, 1,8-octanediol, 1, 10-decanediol, 1,12-dodecanediol, 1,16-hexadecanediol, 1,20-icosanediol, and combinations thereof;
(c) cysteine;
(d) aniline tetramer; and
(e) optionally, a solvent,
wherein the citric acid, polyol, cysteine, and aniline tetramer react together to form the photoluminescent compound.

8. The photoluminescent compound of claim 7, wherein the polyol is 1,8-octanediol.

9. The photoluminescent compound of claim 1, wherein the conductive oligomer is present at 0.1 to 50 mol % relative to the biocompatible multifunctional carboxylic acid compound.

10. The photoluminescent compound of claim 7, having a molecular weight of 500 to 10,000 g/mol.

11. The photoluminescent compound of claim 7, wherein the solvent is selected from the group consisting of dioxane, ethanol, acetone, dimethylformamide, dimethylsulfoxide, and combinations thereof.

12. A film comprising one or more compounds of claim 1.

13. A nanoparticle comprising one or more compounds of claim 1.

14. The nanoparticle of claim 13, wherein the nanoparticle further comprises a drug and/or a targeting molecule.

15. A method for generating an acoustic signal comprising: subjecting a compound of claim 1 to a stimulus comprising electromagnetic radiation, wherein an acoustic signal is generated.

* * * * *